(12) United States Patent
Naka et al.

(10) Patent No.: US 6,180,062 B1
(45) Date of Patent: *Jan. 30, 2001

(54) DEVICE FOR ANALYZING A SAMPLE

(75) Inventors: Michio Naka; Kouji Hirayama, both of Kyoto; Yoshihiko Higuchi; Masufumi Koike, both of Osaka; Hisashi Okuda, Kyoto, all of (JP)

(73) Assignee: Kyoto Daiichi Kagaku Co., Ltd., Kyoto (JP)

( * ) Notice: Under 35 U.S.C. 154(b), the term of this patent shall be extended for 0 days.

This patent is subject to a terminal disclaimer.

(21) Appl. No.: 09/255,253

(22) Filed: Feb. 22, 1999

Related U.S. Application Data

(63) Continuation of application No. 08/847,745, filed on Apr. 22, 1997, now Pat. No. 6,001,307.

(30) Foreign Application Priority Data

Apr. 26, 1996 (JP) ................................................ 8-107310
Sep. 6, 1996 (JP) ................................................ 8-236131

(51) Int. Cl.⁷ ................................................................. G01N 33/48
(52) U.S. Cl. ............................... 422/81; 422/68.1; 436/49
(58) Field of Search ............................... 422/68, 169, 81, 422/82; 436/179

(56) References Cited

U.S. PATENT DOCUMENTS

| | | |
|---|---|---|
| 3,620,676 | 11/1971 | Davis . |
| 4,065,263 | 12/1977 | Woodbridge, III . |
| 4,088,448 | 5/1978 | Lilja et al. . |
| 4,195,526 | 4/1980 | Amos et al. . |
| 4,624,928 | 11/1986 | Qureshi . |
| 4,650,662 | 3/1987 | Goldfinger et al. . |
| 5,120,420 | 6/1992 | Nankai et al. . |
| 5,192,415 | 3/1993 | Yoshioka et al. . |
| 5,262,037 | 11/1993 | Markle et al. . |
| 5,264,103 | 11/1993 | Yoshioka et al. . |
| 5,310,471 | 5/1994 | Markle et al. . |
| 5,354,448 | 10/1994 | Markle et al. . |
| 5,387,327 | 2/1995 | Khan . |
| 5,469,846 | 11/1995 | Khan . |
| 5,575,895 | 11/1996 | Ikeda et al. . |
| 5,582,697 | 12/1996 | Ikeda et al. . |

FOREIGN PATENT DOCUMENTS

| | | |
|---|---|---|
| 1-291153 | 11/1989 | (JP) . |
| 7-167820 | 7/1995 | (JP) . |
| 10-132712 | 5/1998 | (JP) . |

Primary Examiner—Lyle A. Alexander
(74) Attorney, Agent, or Firm—Merchant & Gould P.C.

(57) ABSTRACT

This invention provides a device for analyzing a sample which is capable of performing rapid and precise analysis of a small amount of sample, and whose gradient in a measuring apparatus is not limited. This device comprises approximately a rectangular plate shaped body comprising a base member made of resin and a transparent covering. A first depressed cylindrical concave portion is formed in the upper surface of the base member, and a groove is formed in communication with the first depressed cylindrical concave portion, the groove extending to the end of the protrusion portion 5c, and a second depressed cylindrical concave portion which is smaller than the first depressed cylindrical concave portion is formed in a certain position in the groove, the end of the groove opening to the outside at the end of the protrusion portion 5c. Then, the transparent covering is placed over the upper surface of the base member and then integrated together. As a result, the first depressed cylindrical concave portion, the groove, the second depressed cylindrical concave portion, and the opening at the end of the groove are formed into a suction pressure generating chamber, a drawing channel, an analytical section, and an opening for drawing a sample, respectively.

28 Claims, 22 Drawing Sheets

DEVICE FOR ANALYZING A SAMPLE

This application is a Continuation of application Ser. No. 08/847,745, filed Apr. 22, 1997, now U.S. Pat. No. 6,001,307, which application(s) are incorporated herein by reference.

FIELD OF THE INVENTION

This invention relates to devices for analyzing samples such as body fluids, to methods for analyzing samples by using such devices, and to apparatuses for analyzing samples using such devices.

BACKGROUND OF THE INVENTION

There are various types of samples in the field of analytical chemistry, and particularly in the medical field, body fluids such as blood, urine, spinal fluid, saliva and the like, are important objects for analysis. There are needs for analyzing such samples in large amount and collectively.

In order to meet such needs, a device for analyzing a sample having a reagent film previously impregnated with a reagent, which is stuck on a strip, has been developed and practically used. In such a device, the reagent film is supplied with a sample such as blood, where a component in the sample is reacted with the reagent to generate a pigment, whereby a color is developed in the reagent film, and the color is analyzed by using an optical measuring apparatus such as a densitometer. By using such a device, operations for preparing a reagent and reacting the reagent with a component in the sample can be simplified, thereby the whole process for analyzing a sample becomes a routine exercise.

In such a device, examples of methods for supplying the reagent film with a sample include, methods utilizing capillarity, spotting, dipping, and the like. Among these methods, methods utilizing capillarity have been most commonly used. Because it is required to intercept external light during optical measuring, it is necessary that a sample supplying portion and an analytical section should be positioned away from each other when the device is set in an optical measuring apparatus. Accordingly, a sample is required to be transferred in the device, therefore capillarity is utilized as a means for transferring the sample. Examples of devices utilizing capillarity are those disclosed in Japanese Patent Application Laid-open No. Hei 4-188065 or in Japanese Patent Application Laid-open No. Sho 57-132900.

FIG. 22 shows a device for analyzing a sample utilizing capillarity. As shown in the drawing, the device comprises a triangular shaped sampling point 42 protruding from an approximately center portion of the front face 44 of a transparent base member 47 made of acrylic resin, a groove 46 extending from the sampling point 42 toward the back portion of the base member 47, and a slot 45 formed as an extension of the groove. Furthermore, a reagent film 48 is stuck on the upper face of the base member 47 on the side of the front face 44, so that it may cover over the groove 46. The structure of the reagent film 48 is determined as appropriate depending upon the type of a sample. For example, when analyzing plasma components of blood, a reagent film having a laminated structure comprising a filtration layer, a reagent layer, a transparent protective layer, and an opaque protective layer, which are laminated in this order from the bottom, in which an observation window 50 is formed for entering light in an approximately center portion of the opaque protective layer, is used.

A sample may be analyzed by using such a device as in the following steps. First, a drop of blood is obtained from a subject and brought into contact with the sampling point 42. Then, the blood is introduced into the groove 46 by capillarity and the whole groove is filled with the blood. When the blood permeates into the reagent film 48 covering over the upper portion of the groove 46, erythrocytes are first removed by the filtration layer, and plasma components reach the reagent layer, where a pigment is generated through a reaction between a reagent in the reagent layer and a component in the plasma, whereby a color is developed in the reagent layer. In this state, the device is set in an optical measuring apparatus such as a densitometer, where the color developed in the reagent layer may be measured by irradiating light from the observation window 50.

However, there are problems as described below in using a device utilizing capillarity.

First, because a capillary channel is required to be continuously filled with a sample in order to cause capillarity, an amount of a sample more than required for analysis is needed. In addition, it takes some time to introduce a sample by capillarity, so that measuring cannot be performed quickly. Furthermore, in body fluids such as blood, there are differences among individuals in properties such as viscosity, which affect capillarity, therefore the time period required for introducing a sample into the analytical part or the like cannot be fixed. As a result, it is difficult to fix a time period required for analysis, such as time for reaction with a reagent. Accordingly, there is a possibility that an error might be caused in analysis results. Furthermore, since the drawing force by capillarity is very weak, it is easily affected by gravitational force. Therefore, when introducing a sample, the gradient of the device should be restricted, and the structure of an optical measuring apparatus should also be limited. Furthermore, the sample supplying portion and the analytical section cannot be positioned apart from each other because of the weakness of the drawing force of capillarity, so that possibilities of contamination during an introduction of a sample or influence of external light cannot be completely eliminated in an optical measuring apparatus.

On the other hand, the spotting method has a disadvantage in that when using blood as the sample, the sampling spot is limited to a fingertip, and sampling from an ear or the abdomen is difficult.

SUMMARY OF THE INVENTION

The present invention has been developed in view of the above mentioned background, and an object of the invention is to provide a device capable of performing a rapid and precise analysis of a small amount of a sample, a method for analyzing a sample using such a device, and an apparatus for analyzing a sample using such a device.

In order to solve the above-mentioned problems, the present invention provides a device for analyzing a sample comprising a suction pressure generating means, a drawing channel in communication with the suction pressure generating means, an analytical section formed in a certain position in the drawing channel, and an opening formed at the end of the drawing channel, wherein a sample is introduced from the opening and then drawn into the analytical section through the drawing channel by the suction pressure developed by the suction pressure generating means.

Accordingly, in the device of the present invention, a sample is drawn forcefully by utilizing suction pressure in place of capillarity as used in a conventional device. That is, a suction pressure is developed by the suction pressure generating means, a sample is introduced into the opening by the suction pressure, then the sample is drawn by the suction pressure through the drawing channels into the analytical section, where the sample is analyzed by an optical means, an electrochemical means, or the like. Thus, by using a suction pressure to draw a sample forcefully, it is ensured that a small amount of a sample is introduced into the analytical section. In addition, the time period required for introducing the sample can be fixed to a certain short time, irrespective of the properties of the sample such as viscosity. Accordingly, for example, when analyzing a sample by using a reagent, the time period for reaction between a component in a sample and a reagent can be fixed. In addition, by drawing a sample forcefully, for example, the amount of a sample which is reacted with a reagent can be constantly fixed. Accordingly, errors which might be caused in analysis results can be prevented.

Furthermore, since a sample is drawn forcefully in the device of the present invention, it is not necessary to limit the distance between the sample supplying portion and the analytical section. Therefore, in the device of the present invention, the distance between the sample supplying portion and the analytical section can be longer than in a device utilizing capillarity. Accordingly, influence of external light can be eliminated in an optical measuring apparatus. Therefore, by using the device of the present invention, a small amount of a sample can be analyzed rapidly and precisely. Furthermore, because the sample is drawn forcefully, the influence of gravitational force can be nearly ignored.

In the present invention, by "suction pressure" is understood a pressure for drawing a sample, which is usually a negative pressure.

A sample used in the present invention is not particularly limited as long as it can be sucked, and liquids, sols, or the like are included in the examples. Furthermore, examples of a sample which may be analyzed in the present invention include, whole blood, urine, spinal fluid, blood plasma, serum, saliva, or the like.

Method for analyzing a sample using the device of the present invention are not particularly restricted. For example, an optical means, an electrochemical means or the like can be applied in such methods.

When optical measuring means is applied, either a reagent which reacts with a component in a sample to generate a pigment, or a reagent which reacts with a component in a sample to represent a color in itself is generally used. However, there are some cases in which an analysis may be conducted by using only light transmissivity or light reflectance and without using a reagent. One example of such a case is when analyzing a hematocrit value of blood. Furthermore, instead of measuring transmitted light, other optical means such as measuring reflected light, fluorescence or the like may also be applied.

When electrochemical means is applied, a change in electric current or in electric potential caused by the oxidation-reduction reaction of the sample may be usually measured, and a reagent which causes an oxidation-reduction reaction when reacted with a component in a sample is normally used in such a measurement.

The reagent used in the present invention may be either a dry-type or wet-type reagent. Furthermore, in a device for simultaneous analysis of multiple items (hereinafter referred to as "multiple analysis") as described later, various types of reagents may be usually used depending upon the number of items to be analyzed.

It is preferable that the device of the present invention comprises a plurality of drawing channels, in each of which an analytical section is formed in a certain position, the ends of the drawing channels merging and forming one opening. By using a device having such a structure, simultaneous analysis of multiple items, namely multiple analysis, can be achieved. Such a device is referred to as a device for multiple analysis.

Although suction pressure is utilized for drawing a sample forcefully in the present invention, a suction pressure may also be used in combination with capillarity as described later.

A device for analyzing a sample provided with a bypass channel, and a device for analyzing a sample in which a stopper which is gas-permeable and liquid-impermeable is formed, are preferred embodiments of the present invention. As described above, the device of the present invention has many advantages by utilizing suction pressure for drawing a sample forcefully. However, because such a forced sucking is markedly strong compared to a sucking utilizing capillarity, there is a possibility that a sample might pass through the analytical section and does not remain there. The above embodiments of the present invention provide a solution for such a problem. When using either of the above-described embodiments of the present invention, it is not necessary to be particularly careful when generating a suction pressure, therefore allowing simpler manipulation.

Accordingly, in a first preferred embodiment, a device for analyzing a sample of the present invention includes a suction pressure generating means, a drawing channel in communication with the suction pressure generating means, an analytical section formed in a certain position in the drawing channel, the end of the drawing channel forming an opening, and in addition provided with a bypass channel which branches from a portion of the drawing channel between the analytical section and the opening and is in communication with the suction pressure generating means, wherein the relationship of the liquid flow resistance (X) in the drawing channel between the analytical section and the suction pressure generating means, the liquid flow resistance (Y) in the bypass channel, and the liquid flow resistance (Z) in the drawing channel between the branching portion of the bypass channel and the analytical section is such that X>Y>Z.

In this embodiment, when the developed suction pressure is large, an excess of suction pressure may still remain even after a sufficient amount of a sample has been introduced into the analytical section or the like. In case that an excess of suction pressure remains, there are possibilities that a sample which has been introduced into the analytical section or the like might further be drawn into the suction pressure generating means, that air might be entrained in the analytical section, or that a pigment generated through reaction between a component in the sample and a reagent might flow into the suction pressure generating means. This first preferred embodiment solves such problems by providing a bypass channel, and also by having the relationship of the liquid flow resistance (Y) in the bypass channel and the liquid flow resistances (X, Z) in the two portions of the drawing channel is such that X>Y>Z.

Accordingly, because the liquid flow resistance (Z) in the drawing channel between the branching portion of the bypass channel and the analytical section is the smallest among the three liquid flow resistances (X), (Y), and (Z), even if a suction pressure larger than required is generated by the suction pressure generating means, a sample is first introduced from the opening and drawn into the analytical section in a sufficient amount. In this case, even if an excess amount of a sample and/or entrained air are drawn by the excess suction pressure, the excess of a sample and/or the entrained air can be introduced into the bypass channel, while the sample introduced into the analytical section, a generated pigment and the like remain in the analytical section. This is because the liquid flow resistance (X) in the drawing channel between the analytical section and the suction pressure generating means is larger than the liquid flow resistance (Y) in the bypass channel. Then, the excess of a sample and the entrained air may be discharged into the bypass channel or through the bypass channel into the suction pressure generating means. Accordingly, even if a large suction pressure is generated, it is ensured that a sample is introduced into the analytical section to be analyzed, therefore further rapid and precise analysis of the sample can be achieved.

In the present invention, by "liquid flow resistance" is understood a resistance to flow to which liquid is subjected when moving through a channel, and serves as a criterion for ease of liquid flow.

Suitable methods for controlling the liquid flow resistance in each of the channels are, for example, changing the diameter of the channel, treating the inner surface of the channel which contacts with liquid by using a detergent, a water repellent agent or the like in order to change the wettability. Examples of the water repellent agents are silicon, tetrafluoroethylene resin, and the like.

In order to perform multiple analysis as described above, it is preferable that the first preferred embodiment of the present invention is provided with a plurality of drawing channels, an analytical section formed in a certain position in each of the drawing channels, the ends of the respective drawing channels merging and forming one opening, and a bypass channel branching from a portion of the drawing channel between the merging portion and the opening and being communicated with the suction pressure generating means.

A second preferred embodiment comprises a suction pressure generating means, a drawing channel in communication with the suction pressure generating means, an analytical section formed in a certain position in-the drawing channel, an opening being formed at the end of the drawing channel, and further comprising a stopper which is gas-permeable and liquid-impermeable (hereinafter referred to as a "stopper") formed in a certain position in the drawing channel between the suction pressure generating means and the analytical section, by which a flow of a sample into the suction pressure generating means can be prevented.

In the second embodiments, the portion of the drawing channel between the analytical section and the suction pressure generating means where the stopper may be formed should include both the boundary portion between the drawing channel and the suction pressure generating means, and the boundary portion between the drawing channel and the analytical section.

In the second embodiment, the stopper is usually made of a hydrophobic porous material.

It is preferable that the second embodiment be made for multiple analysis as described below.

That is, in the second embodiment, it is preferable that a plurality of analytical sections are formed in certain position in the drawing channel, and that a stopper is formed in a portion of the drawing channel between the suction pressure generating means and the analytical section which is the closest to the suction pressure generating means.

Furthermore, it is preferable that the second embodiment be provided with a plurality of drawing channels, and an analytical section formed in a certain position in each of the drawing. channels, the ends of the respective drawing channels merging and forming one opening.

It is preferable that the opening of the drawing channel is enlarged toward the end, that is, funnel-shaped. By having such a shape, a sample such as blood can be retained in the opening after the sample is introduced, therefore subsequent drawing operation becomes easier. In addition, air inclusion can also be reduced. Especially in case of sampling blood from a small spot such as a fingertip, it is required to ensure that the opening for the drawing channel in the device is contacted with the sampling spot until introduction of the sample is completed. Therefore, substantial attention is required for controlling sampling, resulting in more complex operation. Furthermore, since an amount of blood which can be obtained from a fingertip or the like is as little as several 10 $\mu$l air inclusion may easily occur in a conventional device for analyzing a sample during introduction of a sample, thereby greatly affecting the measured results. In order to solve such problems, the opening for the drawing channel is formed into a funnel-shape, so that the sample can be retained there. By having such a structure, it is possible to draw the sample through the channel after detaching the opening from the sampling spot, therefore a sample can be easily obtained from a small spot without causing air inclusion.

Furthermore, it is also preferable that the device be provided with a liquid pooling portion formed between the opening and the drawing channel, and an air vent passage branching from a portion of the drawing channel between the liquid pooling portion and the analytical section, the end of the air vent passage opening to the outside of the device. The air vent passage branches from a portion of the drawing channel between the liquid pooling portion and the analytical section so that air inclusion can be prevented during introduction of the sample.

By providing such a liquid pooling portion and an air vent passage, a sample can be introduced by capillarity developed by the air vent passage and retained in the liquid pooling portion, therefore subsequent sucking operation can be performed without causing air inclusion after detaching the opening from the sampling spot.

It is preferable that the liquid flow resistance in the air vent passage is larger than that in the liquid pooling portion, so that air inclusion can be further prevented.

Suitable methods for controlling the liquid flow resistance are, for example, changing the dimension of a cross section, treating the surface which contacts with liquid by using a surface active agent, a water repellent agent or the like to change the wettability. Examples of the water repellent agent include silicon, tetrafluoroethylene resin, and the like. It is preferable that the liquid flow resistance should be controlled by changing dimensions of a cross section in view of controllability. For example, the thickness and the width of the liquid pooling portion may be formed larger than those of the air vent passage.

In the device of the present invention, the analytical section formed in the drawing channel may serve both as a reagent positioning section and a reagent reaction section. Alternatively, a reagent positioning section, a reagent reaction section, and an analytical section may be provided independently in certain positions in the drawing channel. Still alternatively, a plurality of reagent reaction sections, reagent positioning sections, and analytical sections may be provided in certain positions in the drawing channel.

In the device of the present invention, an analytical section preferably serves both as a reagent positioning section and as a reagent reaction section. However, if a reagent can move through the drawing channel, a reagent positioning section, a reagent reaction section, and an analytical section (hereinafter also referred to as a "measuring section") may be independently formed in certain positions in the drawing channel.

In such a device, a sample and a reagent can be mixed and stirred while the sample moves between each of the respective sections, and also in case of using a dry-type reagent, dissolution of the reagent may be facilitated. The reagent may move either independently or together with the sample.

Furthermore, such a device can be applied for multiple steps reaction including a pre-treatment step. For example, if a plurality of reagent reaction sections or the like are provided in series in the drawing channel, a sample can be transferred to the respective sections, while causing reactions respectively. By using such a device, for example, in case of performing analysis utilizing antigen-antibody reaction, in which B/F separation is required, B/F separation can be performed by transferring a sample and a rinsing solution among the respective reagent reaction sections or the like.

Furthermore, in case of using a reagent consisting of two or more components, which cannot be mixed prior to reaction with a sample, it is preferred that a plurality of reagent positioning sections are provided in certain positions in the drawing channel.

Next, in the device for analyzing a sample of the present invention, a suction pressure generating chamber, a suction pressure generating tube or the like capable of changing the volume, may be used as a suction pressure generating means. A vent may be formed in the suction pressure generating chamber.

With regard to the suction pressure generating tube, a suction pressure is generated by drawing the tube through a hand.

In the device of the present invention, when analyzing a sample by using an electrochemical means, it is preferable that the analytical section is provided with a pair of electrodes comprising a working electrode and a counter electrode.

According to another aspect of the present invention, a method for analyzing a sample comprises preparing the device of the present invention, generating a suction pressure by the suction pressure generating means, thereby introducing a sample into the opening, and drawing the sample by the suction pressure through the drawing channel into the analytical section, where analysis of the sample is performed.

A method for analyzing a sample using the first or the second embodiment of the present invention will be described.

A method for analyzing a sample using the first embodiment of the device of the present invention comprises the steps of preparing the first embodiment, developing a suction pressure by the suction pressure generating means, thereby introducing a sample into the opening, and drawing the sample by the suction pressure through the drawing channel into the analytical section, while excess amount of the sample and/or entrained air are discharged into the bypass channel and also through the bypass channel into the suction pressure generating means, thereupon performing an analysis of the sample.

A method for analyzing a sample using the second embodiment comprises the steps of preparing the second embodiment, developing a suction pressure by the suction pressure generating means, thereby introducing a sample into the opening, drawing the sample by the suction pressure through the drawing channel into the analytical section, where analysis of the sample is performed.

When multiple analysis is conducted in these methods, multiple items may be simultaneously analyzed by using a device for multiple analysis.

These methods for analyzing a sample, in which either a device having a funnel-shaped opening or a device provided with a liquid pooling portion and an air vent passage is used, comprise the steps of preparing the device for analyzing a sample, contacting the opening with a sample, thereby drawing the sample into the opening or into the liquid pooling portion by capillarity to retain the sample, and then generating a suction pressure by the suction pressure generating means, drawing the sample retained in the opening or in the liquid pooling portion by the suction pressure through the drawing channel into the analytical section, where analysis of the sample is performed.

According to the method for analyzing a sample using either a device provided with a funnel-shaped opening or a device in which a liquid pooling portion and an air vent passage are formed, for example, the device can be detached from a sampling spot after contacting the opening with a sample in the sampling spot to introduce the sample into the opening or into the liquid pooling portion, where the sample is retained, therefore making the subsequent sucking operation easier.

In these methods for analyzing a sample of the present invention, the means of analysis is not particularly limited, and for example, an optical means or an electrochemical means is used.

Furthermore, apparatus for analyzing a sample of the present invention may be either an optical measuring apparatus or an electric measuring apparatus.

The optical measuring apparatus comprises an optical measuring system provided with a light irradiating section and a light detecting section, and a device for a analyzing a sample, wherein the device is positioned so that the analytical section of the device can be irradiated with light from the light irradiating section, and so that the detecting section can detect transmitted light, fluorescence, or reflected light in the analytical section.

The electric measuring apparatus comprises an electric signal generating means, an electric signal detecting means, and a device for analyzing a sample, wherein the working electrode of the device and the electric signal generating means are connected to each other, and the counter electrode of the device and the electric signal detecting means are connected to each other.

BRIEF DESCRIPTION OF THE DRAWINGS

The above and other objects, features and advantages of the present invention will be apparent from the following detailed description of the preferred embodiments of the invention in conjunction with the accompanying drawings, in which.

DESCRIPTION OF EMBODIMENTS OF THE INVENTION

Next, embodiments of the present invention will be described. In the following embodiments, unless particularly shown otherwise, the analytical section serves both as a reagent positioning section and a reagent reaction section.

EXAMPLE 1

Figure 1A:
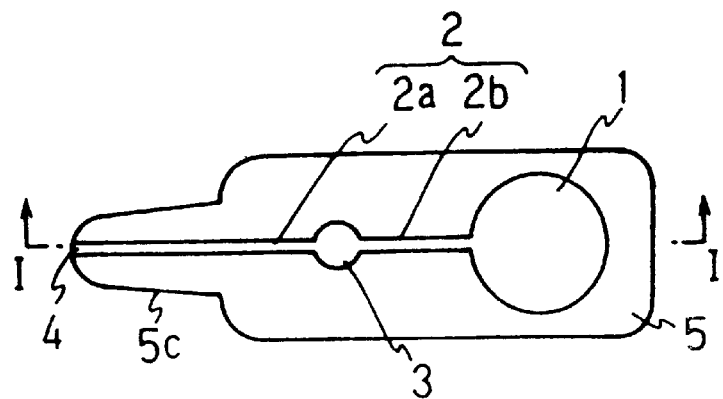
FIG. 1(A) is a plan view of one embodiment of the device for analyzing a sample of the present invention.
Figure 1B:
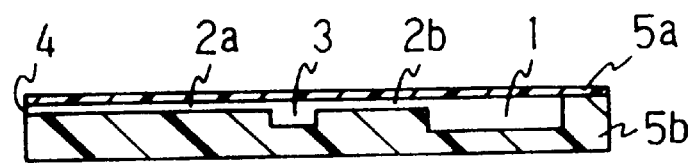
FIG. 1(B) is a cross-sectional view of the device of the FIG. 1(A) taken along the line I—I.

FIG. 1 shows an embodiment of a device for analyzing a sample of the present invention. FIG. 1(A) is a plan view showing such a device, and FIG. 1(B) is a cross-sectional view showing the device of FIG. 1(A) taken along the line I—I.

As shown in the drawings, one end portion of the rectangular plate shaped body 5 (i.e. the left end portion in the drawings) is formed into a protrusion portion 5c which has a smaller width than that of the body. The width of the protrusion portion 5c is decreasing toward the end. Furthermore, the body 5 comprises a base member 5b and a covering 5a which covers over the base member. The base member 5b and the covering 5a are usually integrated together by using an adhesive such as a hot melt adhesive.

In the upper surface side of the base member 5b, a first depressed cylindrical concave portion, which forms a suction pressure generating chamber, is formed in a portion on one end side (right side in the drawings) relative to the center portion, a groove which forms a drawing channel 2 is formed in communication with the first depressed cylindrical concave portion, the groove extending to the end of the protrusion portion 5c, a second depressed cylindrical concave portion which is smaller than the first depressed cylindrical concave portion, which will form an analytical section 3, is formed in a certain position in the groove at an approximately center portion of the body 5, and further the end of the groove opens to the outside at the end of the protrusion portion 5c, thereby forming an opening 4 for drawing a sample. Then, by covering the surface of the base member 5b with a covering 5a and integrating both of them together, the first depressed cylindrical concave portion, the groove, the second depressed cylindrical concave portion, and the end of the groove become the suction pressure generating chamber 1, the drawing channel 2, the analytical section 3, and the opening 4, respectively.

Furthermore, in subsequent embodiments, a suction pressure generating chamber, a drawing channel, a bypass channel, and the like are formed by forming depressed cylindrical concave portions and a groove as in this embodiment.

Although a reagent is not shown in the drawings, when the covering 5a is transparent and light may be irradiated through the covering (from the side of the covering), for example, a reagent film impregnated with a reagent may be stuck on the inner surface of the covering 5a corresponding to the analytical section 3. Furthermore, in the drawings, 2a refers to the portion of the drawing channel 2 between the opening 4 and the analytical section 3, and 2b refers to the portion of the drawing channel 2 between the analytical section 3 and the suction pressure generating chamber 1, respectively.

The dimensions of the device are usually 20 to 50 mm in overall length, 10 to 30 mm in width, 1 to 5 mm in overall thickness, 10 to 20 mm in length of the protrusion portion, 5 to 10 mm in maximum width of the protrusion portion, and 3 to 5 mm in minimum width of the protrusion portion. Furthermore, the dimensions of the suction pressure generating chamber 1 are usually 10 to 20 mm in diameter, 0.2 to 1 mm in depth, and the dimensions of the analytical section 3 are usually 2 to 5 mm in diameter and 0.1 to 0.5 mm in depth. Furthermore, the dimensions of the drawing channel 2 are usually 15 to 40 mm in overall length, 1 to 3 mm in width, and 0.1 to 0.5 mm in depth, in which the drawing channel 2b between the suction pressure generating chamber 1 and the analytical section 3 is 5 to 20 mm in length, and the drawing channel 2a between the analytical section 3 and the opening 4 is 10 to 30 mm in length.

Examples of the material for the base member 5b include acrylonitrile butadiene styrene copolymer (ABS resin), polystyrene, Noryl resin, polyethylene, polyethylene terephthalate (PET), and acrylic resin. It is particularly preferred to use polystyrene or acrylic resin in view of light transmissivity and the like.

It is required that the covering 5a have an elastic property. Moreover, when light is irradiated through the covering, it is also required that at least the portion of the covering corresponding to the analytical section 3 should be transparent. Examples of suitable materials for the covering are PET, polyethylene, and vinyl chloride. In particular, it is preferred to use PET in view of processability and dimensions.

The reagent is usually contained in a reagent film as previously described, and the structure of the reagent film is determined as appropriate depending upon the type of the object for analysis. For example, when plasma components of blood is the object for analysis, a reagent film having a structure in which a filtration layer for separating erythrocytes, a reagent layer impregnated with a reagent, and a base member are laminated in this order is usually used. Furthermore, the reagent film is arranged in the analytical section 3 in such a manner that the filtration layer may contact with blood (the sample), and that irradiating light may enter from the side of the transparent protective layer. In addition, conventionally known materials may be used for the respective layers of the reagent film.

For example, an analysis using this device may be conducted as follows.

First, the portion of the covering 5a corresponding to the suction pressure generating chamber 1 of the device is compressed by applying a pressure, for example, by pressing with a finger.

Then, in this state, the opening 4 at the end of the protrusion portion 5c is contacted with a sample. Then, the pressure applied to the chamber is released by weakening the pressing force with a finger so that the compressed portion of the covering 5a can return to its original shape due to the elasticity of the covering. At this time, a suction pressure is generated, whereby the sample is introduced into the opening 4, and then the sample is further drawn through the drawing channel 2a into the analytical section 3. The time period required for introduction of the sample into the analytical section 3 in this device is markedly short compared to a case of using a device utilizing capillarity. In addition, such time is hardly affected by the properties of the sample such as viscosity. Then, a reaction between a component in the sample and the reagent contained in the reagent film takes place in the analytical section 3 to generate a pigment, whereby a color is developed in the reagent film. Then, the device in which a color is developed in the reagent film is set in a predetermined position in an optical measuring apparatus such as a densitometer. Then, light is irradiated into the device through the covering 5a, whereby when using the densitometer, a reflected light is detected in a detecting section to measure the developed color. When both the base member 5b and the reagent film are also transparent, the sample can also be analyzed by using transmitted light.

EXAMPLE 2

Figure 2:
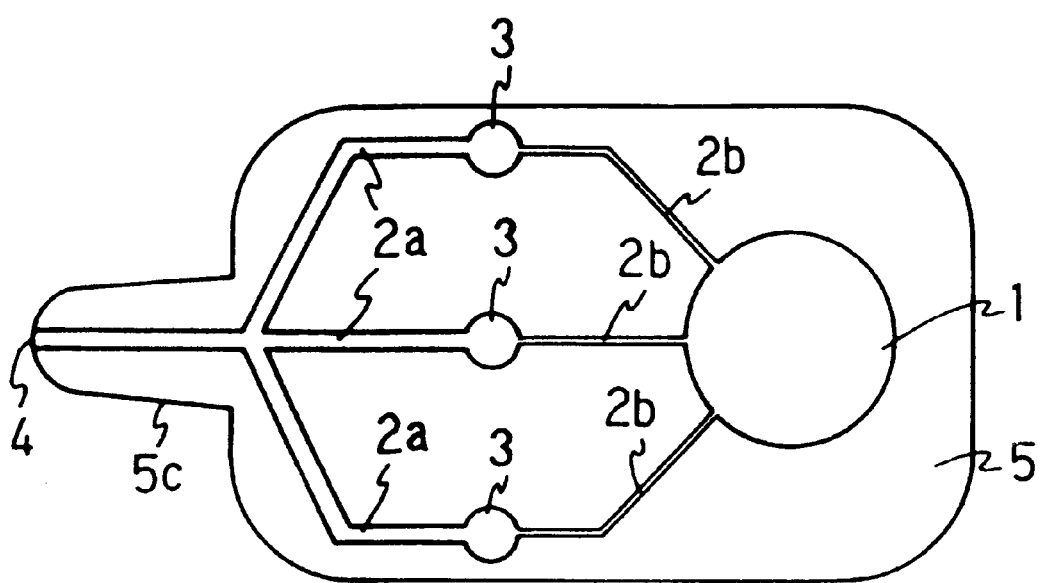
FIG. 2 is a plan view of another embodiment of the device of the present invention.

Next, FIG. 2 is a plan view showing an embodiment of a device for multiple analysis of the present invention. The device for multiple analysis is capable of analyzing three items simultaneously.

As shown in the drawing, one end portion of the rectangular plate shaped body 5 (the left end in the drawing) is formed into a protrusion portion 5c, which is smaller than the body in width in this device. The width of the protrusion portion 5c is decreasing toward the end. Furthermore, the body 5 comprises a base member and a covering which covers over the base member in this device like in the predescribed embodiment.

Like in the device in Example 1, in the upper surface of the base member, three drawing channels 2b extend from a suction pressure generating chamber 1 formed in one end side portion of the body (right side in the drawings) relative to the center of the body. At the end of each drawing channel 2 is formed an analytical section 3, different types of reagents (not shown) being disposed in the respective analytical sections 3, and three drawing channels 2a extend from the respective analytical sections 3, the ends of the drawing channels 2a merging and forming one opening 4. When the covering is transparent, the reagents are disposed by sticking reagent films on the portions of the inner surface of the covering corresponding to the respective analytical sections 3.

In such a device for multiple analysis, overall dimensions are determined as appropriate depending upon the number of the items to be analyzed. Because three items are analyzed in this embodiment, the dimensions of the device are usually 30 to 80 mm in overall length, 20 to 50 mm in width, 1 to 5 mm in overall thickness, 10 to 20 mm in length of the protrusion portion, 5 to 10 mm in maximum width of the protrusion portion, 3 to 5 mm in minimum width of the protrusion portion.

Other things such as the materials, dimensions of the suction pressure generating chamber, the drawing channels and the like, are the same as in the predescribed embodiment of a device for analyzing a sample. Furthermore, the number of items to be analyzed is not particularly limited; however, it is usually between 1 and 20, preferably between 3 and 5. In such a case, various numbers of analytical sections and drawing channels may be formed depending upon the number of the items to be analyzed.

For example, an analysis using such a device for multiple analysis may be performed as follows.

First, a portion of the covering 5a corresponding to the suction pressure generating chamber 1 of the device is compressed by applying a pressure, for example, by pressing with a finger.

Then, in this state, the opening 4 at the end of the protrusion portion is contacted with a sample. Then, the applied pressure to the chamber is released by weakening the pressing force with a finger so that the compressed portion of the covering may return to its original shape due to the elasticity of the covering. At this time, a suction pressure is generated, whereby the sample is drawn into the opening 4 and then further drawn through the three drawing channels 2a to the three analytical sections 3. Like in the embodiment in Example 1, the time period required for the introduction of the sample into the respective analytical sections 3 in this device is markedly short compared to that in a device using capillarity. In addition, the time is hardly affected by the properties of the sample such as viscosity. Then, reactions between components in the sample and the reagents contained in the respective reagent films take place to generate pigments in the respective analytical sections 3, whereby colors are developed in the respective reagent films. Then, the device in which colors are developed in the respective reagent films is set in a predetermined position in an optical measuring apparatus such as a densitometer. Then, light is irradiated into the device, so that when using the densitometer, a reflected light may be detected in a detecting section to measure the developed color, so that three items can be analyzed simultaneously.

EXAMPLE 3

Figure 3:
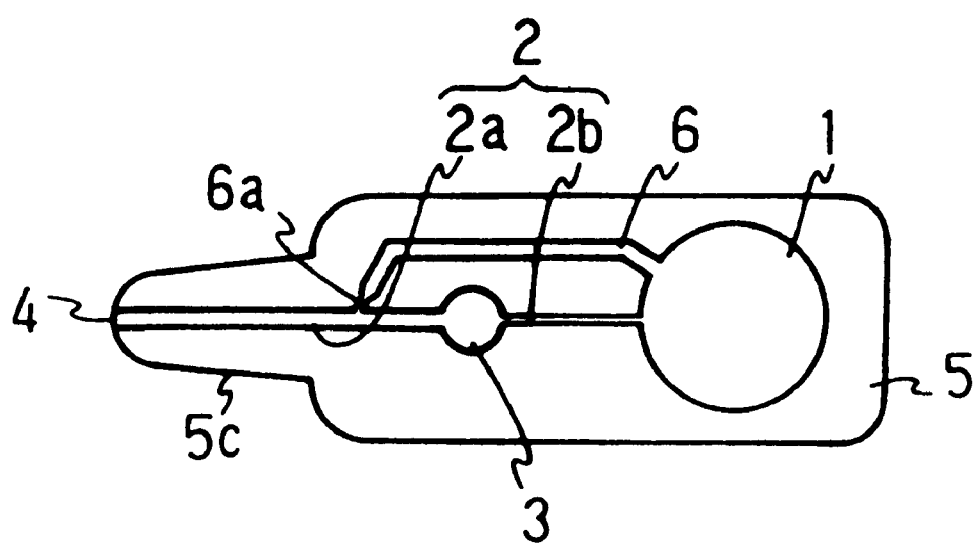
FIG. 3 is a plan view of still another embodiment of the device of the present invention.

FIG. 3 shows a plan view of an embodiment of a device for analyzing a sample of the present invention provided with a bypass channel.

As shown in the drawing, one end side portion of the rectangular plate shaped body 5 (the left end in the drawing) is formed into a protrusion portion 5c, which is smaller than the body in width. The width of the protrusion portion 5c is decreasing toward the end. Furthermore, the body 5 comprises a base member and a covering which covers over the base member in the device like in the predescribed embodiment.

Like in the embodiment in Example 1, in the upper surface of the base member 5b, a drawing channel 2b extends from a suction pressure generating chamber 1 formed in one end side portion of the body 5 (right side in the drawing) relative to the center of the body. At the end of the drawing channel 2b is formed an analytical section 3, and a reagent (not shown) is disposed in the analytical section 3, and further a drawing channel 2a extends from the analytical section 3 toward the end of the protrusion portion 5c. At the end of the drawing channel 2a is formed an opening 4. Where the covering is transparent, the reagent is disposed by sticking a reagent film on a portion of the inner surface of the covering corresponding to the analytical section 3. A bypass channel 6 branches from a portion of the drawing channel 2a between the opening 4 and the analytical section 3, and extends to communicate with the suction pressure generating chamber 1.

Furthermore, the relationship among three liquid flow resistances, namely, the liquid flow resistance (X) in the drawing channel 2b between the suction pressure generating chamber 1 and the analytical section 3, the liquid flow resistance (Y) in the bypass channel, and the liquid flow resistance (Z) in the drawing channel 2a between the branching portion of the bypass channel 6 and the analytical section 3 is such that X>Y>Z.

As shown in the drawing, the entire drawing channel 2a has a large diameter, so that the liquid flow resistance (Z) is the smallest among the three, the bypass channel 6 includes a certain length of a channel 6a having a small diameter extending from the branching portion, so that the liquid flow resistance (Y) is the second smallest, and the entire drawing channel 2b has a small diameter, so that the liquid flow resistance (X) is the largest.

The drawing channel 2a is usually 10 to 30 mm in length, 1 to 3 mm in width, 0.1 to 0.5 mm in depth. The bypass channel 6 is usually 10 to 30 mm in overall length, wherein the bypass channel 6a having a small diameter is 0.5 to 5 mm in length, 0.1 to 0.5 mm in width, and 0.1 to 0.5 mm in depth, and also the portion of the bypass channel having a large diameter is 1 to 3 mm in width and 0.1 to 0.5 mm in depth. The drawing channel 2b is usually 0.5 to 30 mm in length, 0.1 to 0.5 mm in width, and 0.1 to 0.5 mm in depth.

In such a device having the bypass channel 6, the overall dimensions, materials, dimensions of the suction pressure generating chamber and the like, and so forth, are the same as those of the device in Example 1.

Figure 4:
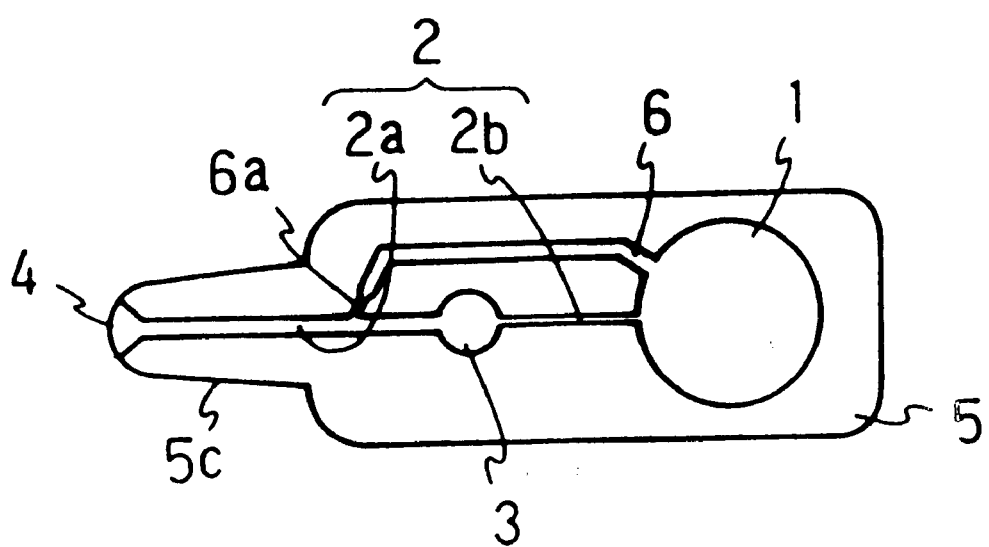
FIG. 4 is a plan view of still another embodiment of the device of the present invention.

Next, FIG. 4 shows a plan view of an embodiment of a device having the bypass channel 6 in which the channel 6a having a small diameter is relatively long. In such a device, the bypass channel 6 is usually 10 to 30 mm in overall length, wherein the bypass channel 6a having a small diameter is 3 to 10 mm in length, 0.1 to 0.5 mm in width, and 0.1 to 0.5 mm in depth, and also the portion of the bypass channel having a large diameter is 1 to 3 mm in width and 0.1 to 0.5 mm in depth. By having such a relatively long bypass channel 6a having a small diameter, it is possible to provide a large difference between the liquid flow resistance (Y) in the bypass channel 6 and the liquid flow resistance (Z) in the drawing channel 2a between the branching portion of the bypass channel 6 and the analytical section 3.

In the device shown in FIG. 4, the width of the opening 4 is increasing toward the end, that is, funnel-shaped. By having such a shape, a sample can be retained in the funnel-shaped opening 4 during sampling, therefore the subsequent sucking operation can be performed smoothly, while air inclusion can be prevented. The opening 4 is usually 3 to 6 mm in maximum width, 1 to 3 mm in minimum width, and 1 to 5 mm in length.

Other than the bypass channel 6 and the opening 4, the structure of the device shown in FIG. 4 is the same as that of the device shown in FIG. 3.

An analysis using such a device having a bypass channel (FIG. 3 or 4) is conducted, for example, as follows.

Figure 5A:
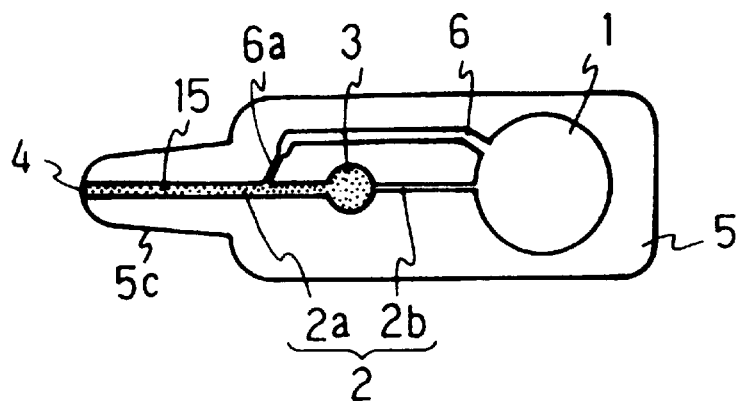
FIGS. 5(A)–5(D) are plan views showing a stepwise process for drawing a sample in one embodiment of the device of the present invention in which a bypass channel is provided.
Figure 5B:
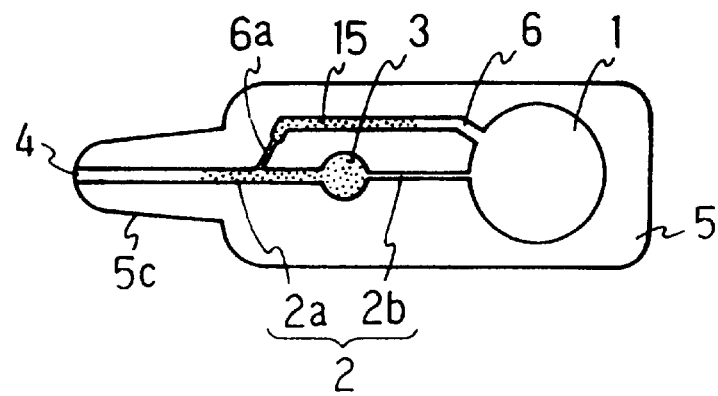
Figure 5C:
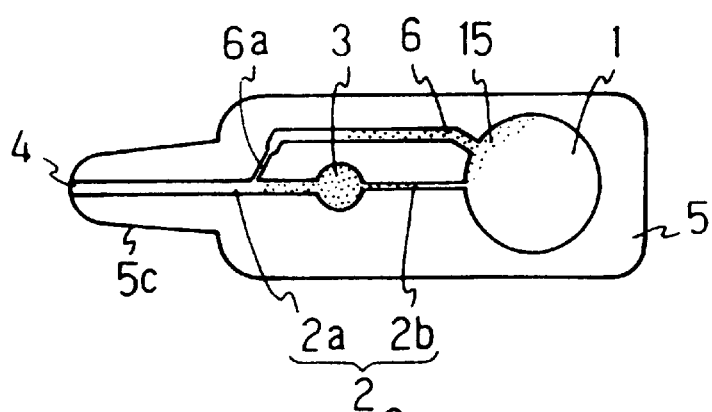

First, a portion of the covering corresponding to the suction pressure generating chamber 1 of the device is compressed by applying a pressure, for example, by pressing with a finger. Then, in this state, the opening 4 at the end of the protrusion portion 5c is contacted with a sample. Then, in this state, the pressure applied to the chamber is released by weakening the force of pressing with a finger, so that the compressed portion of the covering can return to its original shape due to the elasticity of the covering. At this time, a suction pressure is developed, and if the developed suction pressure is larger than required, the sample is drawn in a manner, such as shown in FIG. 5. That is, because the liquid flow resistance (Z) in the drawing channel 2a between the branching portion of the bypass channel 6 and the analytical section 3 is the smallest among the three liquid stresses as described above, a sample 15 is first introduced into the opening 4 and further drawn through the drawing channel 2a into the analytical section 3 as shown in FIG. 5(A). If an excess of suction pressure still remains, because the liquid flow resistance (Y) in the bypass channel 6a is smaller than the liquid flow resistance (X) in the drawing channel 2b, an excess amount of the sample 15 and/or entrained air will flow into the bypass channel 6 as shown in FIG. 5(B), and further part of them may flow into the suction pressure generating chamber 1 as shown in FIG. 5(C). At this time, because the liquid flow resistance (X) in the drawing channel 2b is the largest of the three, the sample introduced into the analytical section 3 remains there, where a reaction between a component in the sample and a reagent (not shown) takes place to generate a pigment, thereby developing a color in the reagent film. In addition, a possibility that the pigment might flow into the suction pressure generating chamber 1 can be eliminated.

Figure 5D:
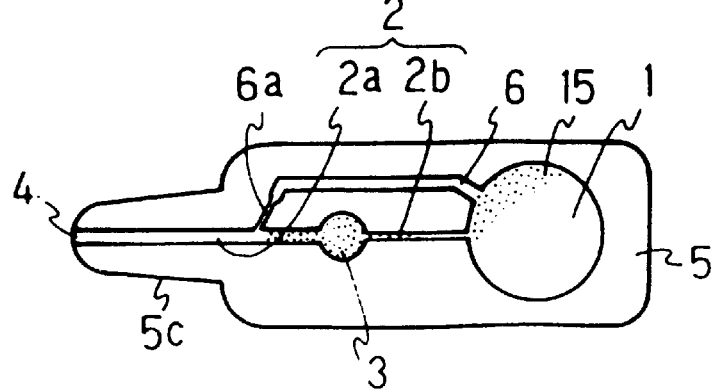

Furthermore, if an excess of suction pressure still remains, the excess amount of the sample 15 and/or entrained air present in the bypass channel 6 is further discharged into the suction pressure generating chamber 1 as shown in FIG. 5(D).

Then, the device in which a color is developed in the reagent film is set in a predetermined position in an optical measuring apparatus such as a densitometer. Then, light is irradiated into the device, so that when using the densitometer, reflected light is detected in a detecting section to measure the developed color.

Thus, by having the bypass channel in the device and also providing said relationship of the liquid stresses in the three portion of the channels, even if excess suction pressure is developed, the sample is ensured to be introduced into the analytical section, where the sample undergoes reaction with a reagent. Moreover, a possibility of overflow of the generated pigment can be eliminated. Accordingly, by using such a device having a bypass channel, rapid sampling can be conducted without carefully adjusting the force of pressing with a finger.

EXAMPLE 4

Figures 6A, 6B:
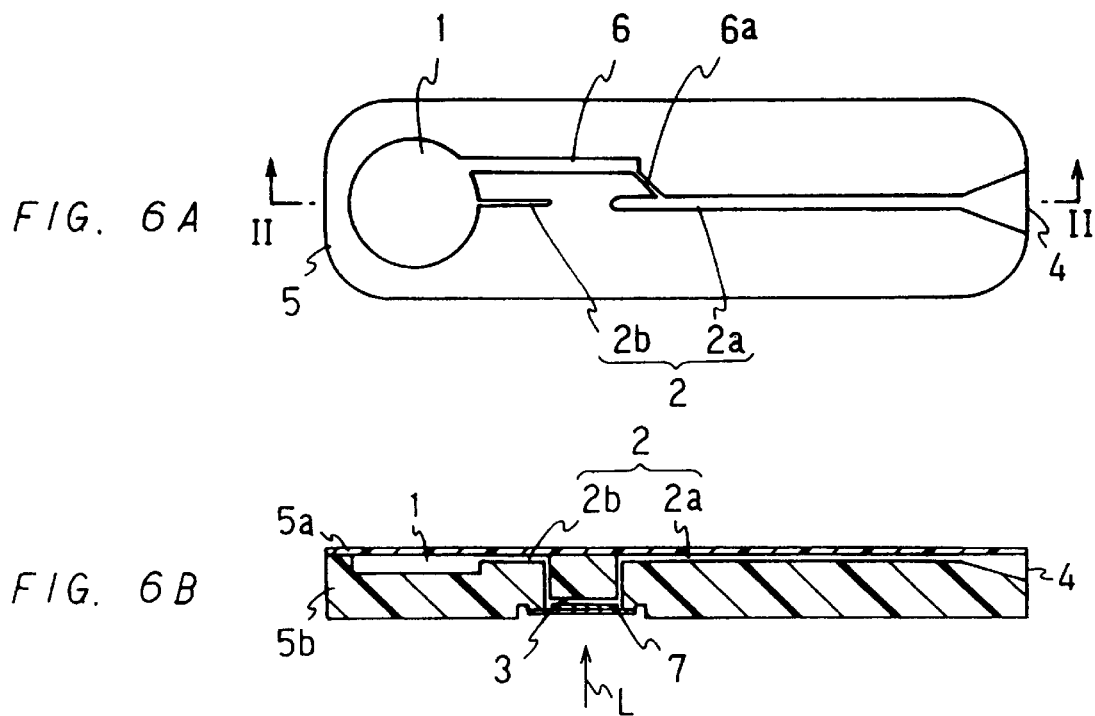
FIG. 6(A) is a plan view of still another embodiment of the device of the present invention.
FIG. 6(B) is a cross-sectional view of the device of the FIG. 6(A) taken along the line II—II.

FIG. 6 shows an embodiment of a device for analyzing a sample of the present invention in which an analytical section is formed in the under surface side of the body. In this device, light is irradiated from the under surface side of the body. FIG. 6(A) is a plan view of such a device, and FIG. 6(B) is a cross-sectional view of the device in FIG. 6(A) taken along the line II—II.

As shown in the drawings, this device comprises an approximately rectangular plate shaped body 5, the body 5 comprising a base member 5b and a covering 5a which covers over the surface of the base member.

In the upper surface of the base member 5b, a suction pressure generating chamber 1 is formed in a portion on one end side of the body 5 (left side in the drawings) relative to the center of the body 5, from which a drawing channel 2b extends toward the other end side of the body. Then, the drawing channel 2b extends downwards from the upper surface side to the under surface side of the base member, where the channel communicates with one end side of the analytical section 3 formed in the under surface side of the base member 5b. As shown in the drawings, a reagent film 7 is disposed in the analytical section 3. Then, a drawing channel 2a extends from the other end side of the analytical section 3 to reach the upper surface side of the base member 5b, and then further extends toward the other end side of the body (the opposite side to the suction pressure generating chamber 1) in the upper surface side of the base member 5b, the end of the channel forming an opening 4. The opening 4 is formed into a funnel shape. Furthermore, a bypass channel 6 also extends from the suction pressure generating chamber 1, the end of the bypass channel merging into the drawing channel 2a between the analytical section 3 and the opening 4. A portion of the bypass channel 6 from the merging portion is formed to be a bypass channel 6a having a small diameter, while the whole drawing channel 2b has a small diameter, and the whole drawing channel 2a has a large diameter. As a result, the relationship of the liquid flow resistance (X) in the drawing channel 2b, the liquid flow resistance (Y) in the bypass channel 6a, and the liquid flow resistance (Z) in a portion of the drawing channel 2a between the branching portion of the bypass channel 6 and the analytical section 3 is X>Y>Z.

In this device, the covering 5a is not necessarily transparent, however, it may be transparent so that the process of drawing a sample can be observed.

Furthermore, the materials of the base member 5b and the covering 5a, the dimensions of the suction pressure generating chamber, the drawing channel, and the like in the device are the same as in the device of the embodiment previously described.

Next, an analysis using such a device is conducted, for example, as follows.

First, a portion of the covering 5a corresponding to the suction pressure generating chamber 1 of the device is compressed by applying a pressure, for example, by pressing with a finger. Then, in this state, the opening 4 is contacted with a sample.

Then, the pressure applied to the chamber is released by weakening the force of pressing with a finger so that the compressed portion of the covering 5a can return to its original shape due to the elasticity of the covering. At this time, a suction pressure is generated, whereby the sample is drawn into the opening 4, and then further drawn through the drawing channel 2a into the analytical section 3. By having the bypass channel 6 and providing the relationship of the three liquid flow resistances (X,Y,Z) of X>Y>Z in this device, even if excess suction pressure is generated, the sample is ensured to be introduced into the analytical section 3, where the sample undergoes reaction with a reagent. In addition, a possibility that a generated pigment might flow into the suction pressure generating chamber 1 can be eliminated. Then, the device in which a color is developed in the reagent film is set in a predetermined position in an optical measuring apparatus such as a densitometer. Then, light L is irradiated into the device from the under surface side of the base member 5b, so that when using the densitometer, a reflected light is detected in a detecting section to measure the developed color.

EXAMPLE 5

Figure 7:
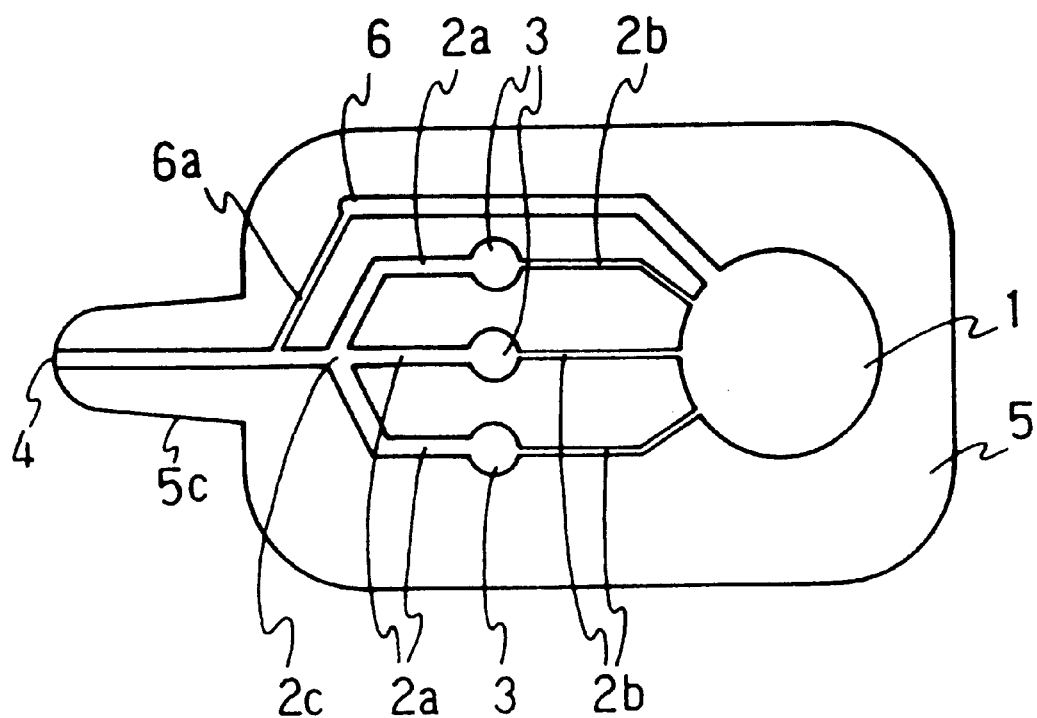
FIG. 7 is a plan view of still another embodiment of the device of the present invention.

Next, FIG. 7 shows a plan view of an embodiment of a device for multiple analysis of the present invention. This device for multiple analysis is capable of analyzing three items simultaneously.

As shown in the drawing, one end portion of the rectangular plate shaped body 5 (the left end in the drawing) in this device is formed into a protrusion portion 5c, which is smaller than the body in width. The width of the protrusion portion 5c is decreasing toward the end. Furthermore, the body 5 comprises a base member and a covering which covers over the surface of the base member as in the predescribed embodiment.

In the upper surface of the base member, three drawing channels 2b extend from a suction pressure generating chamber 1 formed in one end side portion of the body (right side in the drawing) relative to the center of the body. At each end of the respective drawing channels 2b is formed an analytical section 3, different types of reagents (not shown) being disposed in the respective analytical sections 3, and three drawing channels 2a extend from the respective analytical sections 3, the ends of the respective drawing channels 2a merging into one opening 4. When the covering is transparent, the reagents are disposed by sticking reagent films on the inner surface of the covering corresponding to the respective analytical sections 3. A bypass channel 6 extends from the suction pressure generating chamber 1, the end of the bypass channel merging into the opening 4. A certain portion of the bypass channel 6 from the merging portion is formed as a bypass channel 6a having a small diameter, while the whole drawing channels 2b have small diameters, and the whole drawing channels 2a have large diameters. As a result, the relationship of the liquid flow resistance (X) in the drawing channels 2b, the liquid flow resistance (Y) in the bypass channel 6, and the liquid flow resistance (Z) in the portions of the drawing channels 2a between the branching portion of the bypass channel 6 and the analytical sections 3 is X>Y>Z.

In such a device for multiple analysis, the overall dimensions are determined as appropriate depending upon the number of the items to be analyzed. Because three items are to be analyzed in this embodiment, the dimensions of the device are usually 20 to 50 mm in overall length, 20 to 50 mm in width, and 1 to 5 mm in overall thickness, wherein the protrusion portion is 10 to 20 mm in length, 5 to 20 mm in maximum width, 3 to 5 mm in minimum width. Other things such as materials, dimensions of the suction pressure generating chamber, the drawing channels and the like, and so forth in-this device are the same as in the device of prescribed embodiment having a bypass channel. Furthermore, the number of items to be analyzed is not particularly limited, however, it is usually between 1 and 20, preferably between 3 and 5. In this case, various number of analytical sections, bypass channels and drawing channels may be formed depending upon the number of the items to be analyzed.

An analysis using such a device for multiple analysis may be performed, for example, as follows.

First, a portion of the covering 5 corresponding to the suction pressure generating chamber 1 of the device is compressed by applying a pressure, for example, by pressing with a finger.

Then, in this state, the opening 4 at the end of the protrusion portion is contacted with a sample. Then, the pressure applied to the chamber is released by weakening the force of pressing with a finger so that the compressed portion of the covering can return to its original shape due to the elasticity of the covering. At this time, a suction pressure is developed, whereby the sample is drawn into the opening 4 and then further drawn through the three drawing channels 2a into the respective three analytical sections 3. By having the bypass channel 6 and providing the relationship of the three liquid flow resistances (X,Y,Z) of X>Y>Z in this device, even if excess suction pressure is generated, the sample is ensured to be introduced into the analytical sections 3, where the sample undergoes reaction with a reagent, in addition, a possibility that a generated pigment might flow into the suction pressure generating chamber 1 can be eliminated. Then, the device in which a color is developed in the reagent film is set in a predetermined position in an optical measuring apparatus such as a densitometer. Then, light is irradiated into the device, so that when using the densitometer, a reflected light is detected in a detecting section to measure the developed color, so that three items can be analyzed simultaneously.

EXAMPLE 6

Figure 8:
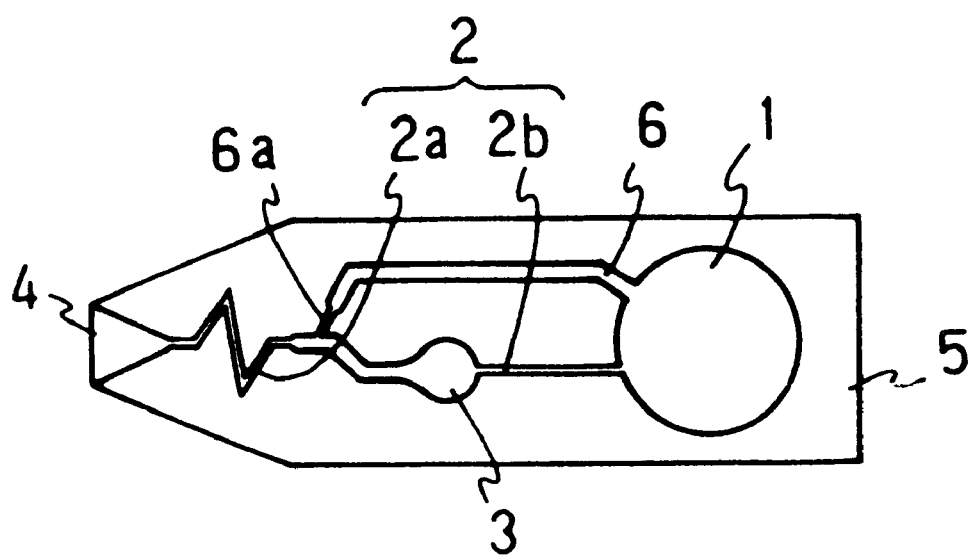
FIG. 8 is a plan view of still another embodiment of the device of the present invention.

FIG. 8 shows a plan view of an embodiment of a device for analyzing a sample in which a portion of a drawing channel between an opening and a branching portion of a bypass channel snakes and also has a small diameter, so that the liquid stress in the portion of the drawing channel becomes the largest.

As shown in the drawing, this device comprises an approximately rectangular plate shaped body 5 whose one end portion is decreasing in width toward the end, and the body 5 comprises a base member and a covering which covers over the surface of the base member.

Then, in the upper surface of the base member, a suction pressure generating chamber 1 is formed in a portion on the other end side (right side in the drawing) relative to the center of the body 5, from which a drawing channel 2b extends toward the one end portion of the body having decreasing width. An analytical section 3 is formed in a certain position in the drawing channel 2b (in an approximately center portion of the body 5). Then, a drawing channel 2a extends from the analytical section 3 toward the portion of the body having decreasing width, and the drawing channel 2a snakes from a certain point. Furthermore, a bypass channel 6 branches from the drawing channel 2a, and it is brought to be communicated with the suction pressure generating chamber 1. Furthermore, as previously described, the drawing channel 2a snakes from the branching portion of the bypass channel 6, and the end of the drawing channel 2a is formed into a funnel-shaped opening 4 on the end portion of the body having decreasing width. A reagent is disposed in the analytical section 3, and when the covering is transparent, the reagent is disposed by sticking a reagent film containing the reagent on a portion of the inner surface of the covering corresponding to the analytical section 3.

The whole portion of the drawing channel 2a between the branching portion of the bypass channel 6 and the analytical section 3 is made to have a large diameter, and a portion 6a of certain length from the branching portion of the bypass channel 6 is made to have a small diameter, and the whole drawing channel 2b is made to have a small diameter. The snaking portion of the drawing channel 2a is made to have a small diameter and to be longer than the drawing channel 2b. Thus, the liquid flow resistance (W) in the snaking portion of the drawing channel 2a is larger than the liquid flow resistance (X) in the drawing channel 2b. Accordingly, the relationship of the four liquid flow resistances, namely, the liquid flow resistance (W) in the snaking portion of the drawing channel 2a, the liquid flow resistance (X) in the drawing channel 2b, the liquid flow resistance (Y) in the bypass channel 6, and the liquid flow resistance (Z) in a portion of the drawing channel 2a between the branching portion of the bypass channel 6 and the analytical section 3 is such that W>X>Y>Z.

In such a device, the snaking portion of the drawing channel 2a is usually 5 to 15 mm in overall length, 0.1 to 0.5 mm in width, and 0.1 to 0.5 mm in depth. Other things such as materials, the dimensions of the suction pressure generating chamber and other portions of the drawing channels, and the like are the same in this device as those in the predescribed embodiment.

Next, an analysis using such a device is performed, for example, as follows.

First, a portion of the covering 5a corresponding to the suction pressure generating chamber 1 of the device is compressed by applying a pressure, for example, by pressing with a finger. Then, in this state, the opening 4 at the end of the protrusion portion is contacted with a sample. Then, the pressure applied to the chamber is released by weakening the force of pressing with a finger, so that the compressed portion of the covering 5a can return to its original shape due to the elasticity of the covering. At this time, a suction pressure is developed, whereby a sample is drawn into the opening 4. Because the relationship of the four liquid flow resistances (W, X, Y, Z) is W>X>Y>Z, even if a strong suction pressure is developed, it is ensured that the sample is further introduced into the analytical section 3, where the sample is analyzed. Furthermore, because the liquid flow resistance (W) in the snaking portion of the drawing channel 2a is the largest, possibilities that the sample introduced into the analytical section 3 and/or a generated pigment might flow out toward the side of the opening 4 is reduced. Then, the device in which a color is developed in the reagent film is set in a predetermined position in an optical measuring apparatus such as a densitometer. Then, light is irradiated into the device from the upper surface side of the body 5, so that when using the densitometer, a reflected light is detected in a detecting section to measure the developed color.

EXAMPLE 7

Figure 9A:
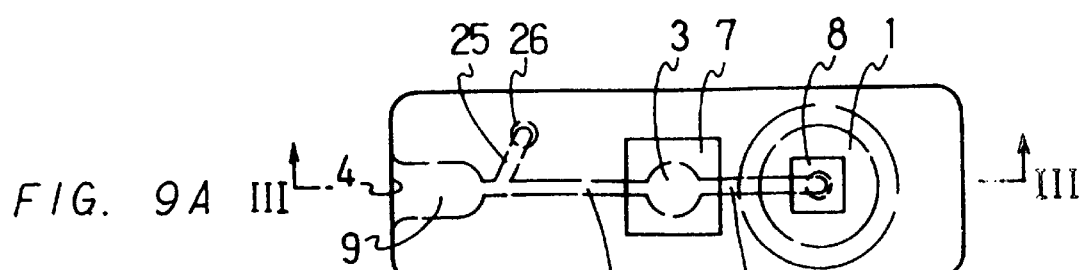
FIG. 9(A) is a plan view of still another embodiment of the device of the present invention.
Figure 9B:
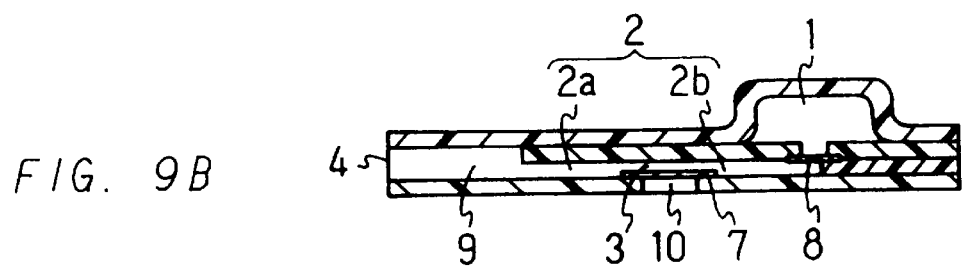
FIG. 9(B) is a cross-sectional view of the device of the FIG. 9(A) taken along the line III—III.

FIG. 9 shows an embodiment of a device for analyzing a sample of the present invention. FIG. 9(A) is a plan view of such a device, and FIG. 9(B) is a cross-sectional view of the device of FIG. 9(A) taken along the line III—III. As shown in the drawings, this device is formed by lamination of a plurality of films, and the body of the device is an approximately rectangular plate shaped.

In this device, a suction pressure generating chamber 1 is formed as a protrusion in a portion of one end side (right side in the drawings) relative to center of the approximately rectangular plate shaped body. A drawing channel 2 extends from under side of the suction pressure generating chamber 1 toward the end opposite to the suction pressure generating chamber 1 (the other end) of the approximately rectangular plate shaped body. An analytical section 3 is formed in a certain position in the drawing channel 2, and the end of the drawing channel 2 communicates with the opening 4 formed in the other end of the approximately rectangular plate shaped body through a liquid pooling portion 9. A window 10 is formed under the analytical section 3, if the need arises. For example, if using glucose oxidase (GOD) as a reagent, because the reagent requires oxygen for coloring reaction, the window should be formed for supplying oxygen. However, except in such a case, when the portion of the film corresponding to the analytical section 3 is transparent so that light can enter into the analytical section 3, it is not required to form the window. Furthermore, a reagent film 7 impregnated with a reagent is disposed under the analytical section 3, so that it covers the window 10. Furthermore, a stopper which is gas-permeable and liquid-impermeable 8 is formed in a certain position in the drawing channel 2b between the suction pressure generating chamber 1 and the analytical section 3 on the side of the suction pressure generating chamber 1. The stopper 8 is formed by disposing a hydrophobic porous film in a certain position in the drawing channel 2b.

Furthermore, an air vent passage 25 branches from a portion of the drawing channel 2a between the liquid pooling portion 9 and the analytical section 3, and the end 26 of the passage is open to the outside of the body. By providing such an opening, capillarity can be developed because of the air vent passage 25.

Furthermore, the area of the cross section of the air vent passage 25 is made smaller than that of the cross section of the liquid pooling portion 9, so that the liquid flow resistance in the air vent passage 25 is larger than that in the liquid pooling portion 9. Specifically, the liquid pooling portion 9 is about four times as wide as the drawing channel 2 or the air vent passage 25, and the liquid pooling portion 9 is about twice as thick as the drawing channel 2 or the air vent passage 25.

Figure 10:
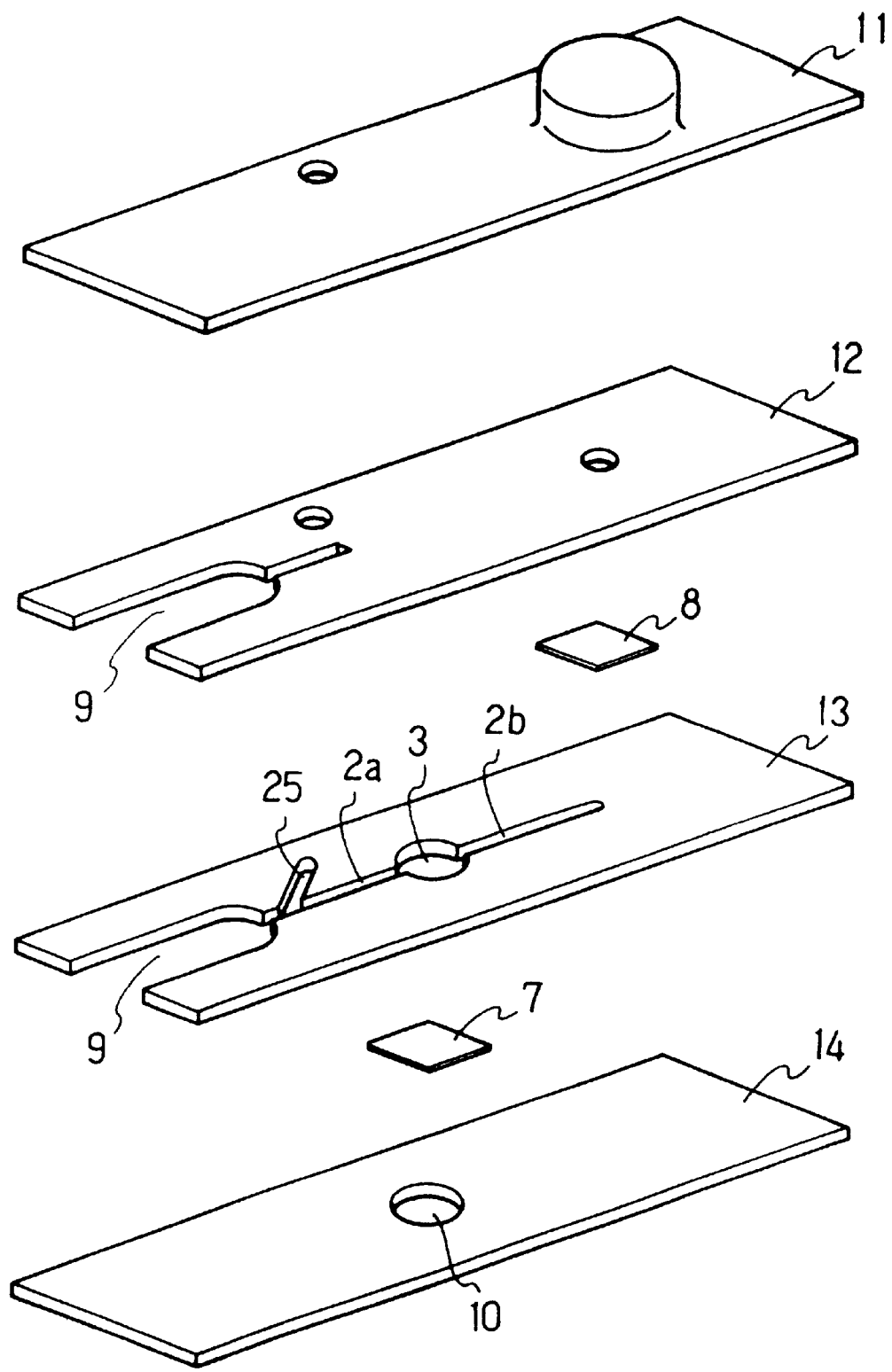
FIG. 10 is a perspective view showing the fabrication of the device shown in FIG. 9.

Such a device of laminated films can be produced, for example, by laminating films 11, 12, 13, and 14 formed into respective types of shapes, with a reagent film 7 and a hydrophobic porous film 8 placed therebetween, as shown in FIG. 10.

The film 14 is to be the under surface of the device, wherein the window 10 is provided. In the film 13 are formed cutout portions to form the liquid pooling portion 9, the air vent passage 25, the analytical section 3, and the drawing channel 2, respectively. The film 12 ensures the thickness of the liquid pooling portion 9 (the size of the cross-sectional area of the portion). In the film 12 are formed a cut-out portion in order to form the liquid pooling portion 9, a circular shaped cut-out portion in order to form an opening at the end of the air vent passage 25, and a circular shaped cut-out portion in order to communicate the drawing channel 2b with the suction pressure generating chamber 1. In the film 11 are formed a protrusion of an approximately cylindrical convex portion in order to form the. suction pressure generating chamber 1 and a circular cut-out portion in order to form an opening at the end of the air vent passage 25.

Then, the reagent film 7 is disposed in a portion between the film 14 and the film 13 where the analytical section 3 is to be formed, and the hydrophobic porous film 8 is disposed between the film 13 and the film 12 in a portion to be a part of the drawing channel 2b. In this state, the four films 14, 13, 12, and 11 are laminated in this order from the bottom and then integrated together to produce a device as shown in FIG. 9.

An example of the hydrophobic porous film is a hydrophobic resin porous film, specifically, a polyethylene porous film, a polypropylene porous film, a Teflon porous film, or the like. Suitable hydrophobic resin porous films are Celgard (Product Name/Hoechst Celanese Co., Ltd.), and Hipore (Product Name/Asahi Chemical Industry Co., Ltd.). The average diameter of a pore in the hydrophobic resin porous film is usually from 0.1 to 1 $\mu$m, preferably from 0.3 to 0.7 $\mu$m. Furthermore, the thickness of the hydrophobic resin porous film is usually from 10 to 100 $\mu$m. Such a hydrophobic resin porous film can be produced, for example, by forming a film using said hydrophobic resin and then orienting the film either uniaxially or biaxially.

The reagent film 7 is a film impregnated with a reagent, and the type of the reagent is selected as appropriate depending upon the type of the object for analysis. The structure of the reagent film is also determined as appropriate depending upon the type of the object to be analyzed. For example, when plasma components of blood is the object for analysis, the reagent film usually has a structure in which a filtration layer for separating blood cells, a reagent layer impregnated with a reagent, and a base member are laminated in this order. Then, the reagent film 7 is arranged in the analytical section 3 so that the filtration layer can contact with blood (a liquid sample). Moreover, conventionally known materials can be applies for the respective layers in the reagent film.

When producing a device of the present invention, the films may be integrated by using an adhesive to bond the respective films to each other or by laminating the films by pressing or heating.

Furthermore, suitable materials for the films which comprise the device are, for example, polyethylene, polyethylene terephthalate (PET), polystyrene, polyvinyl chloride, and the like, and particularly PET is desired because of processability.

The dimensions of the device shown in FIG. 9 are usually 15 to 60 mm in length, 5 to 20 mm in width, and 1 to 3 mm in thickness. Furthermore, the dimensions of the suction pressure generating chamber 1 are usually 3 to 15 mm in diameter and 0.5 to 3 mm in height. Furthermore, the dimensions of the drawing channel 2 are usually 10 to 40 mm in overall length, 0.5 to 2 mm in width, and 0.1 to 0.5 in thickness, wherein the drawing channel 2a is 5 to 30 mm in length, and the drawing channel 2b is 5 to 30 mm in length. Furthermore, the dimensions of the analytical section 3 are usually 2 to 10 mm in diameter and 0.1 to 1 mm in height. The dimensions of the liquid pooling portion 9 are usually 2 to 10 mm in length, 2 to 10 mm in width, and 0.2 to 1 mm in thickness. The dimensions of the air vent passage 25 are usually 2 to 10 mm in overall length, 0.5 to 2 mm in width, 0.1 to 0.5 mm in thickness, and 0.5 to 5 mm in diameter of the opening of the passage. The dimensions of the opening 4 are usually 2 to 10 mm in width and 0.2 to 1 mm in thickness.

Next, a method for analyzing a sample using the device shown in FIG. 9 will be described by referring to FIG. 11. In FIG. 11, the same parts as shown in FIG. 9 are referred to by using the same signs.

Figure 11A:
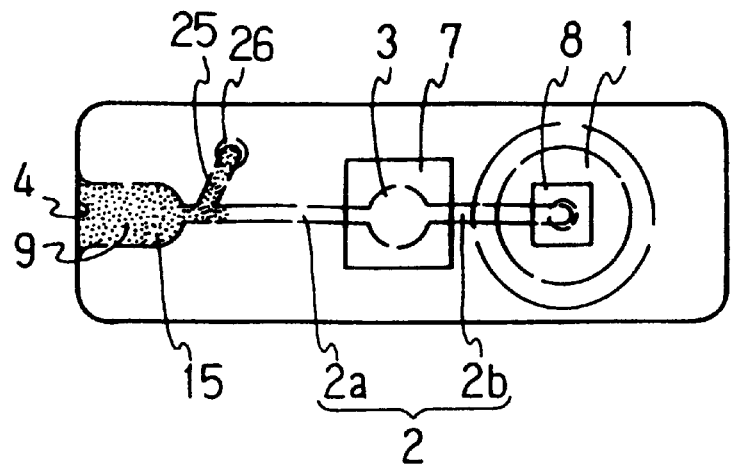
FIG. 11(A) is a plan view of the device shown in FIG. 9, in which a sample is introduced and retained in the liquid pooling portion.
Figure 11B:
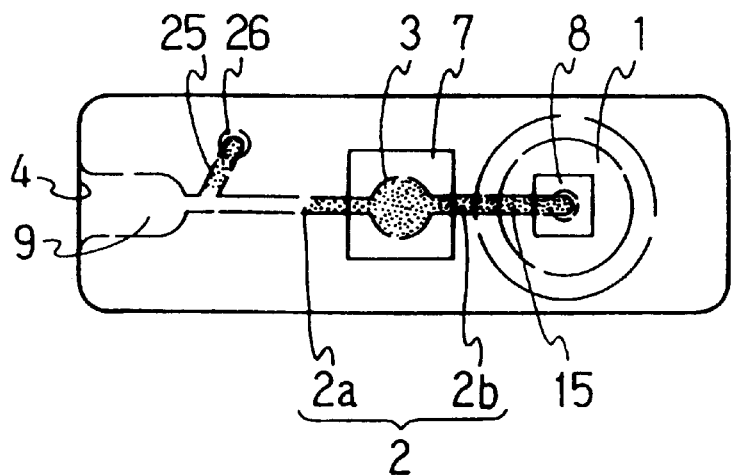
FIG. 11(B) is a plan view of the device shown in FIG. 9, in which a sample is drawn into the analytical section.

First, the protruding suction pressure generating chamber 1 in the device is compressed by applying pressure, for example, by pressing with a finger. Then, in this state, the opening 4 is contacted with a sample 15 in a predetermined sampling spot. Then, as shown in FIG. 11(A), the sample 15 is drawn by capillarity developed due to the air vent passage 25 into the opening 4 and retained in the liquid pooling portion 9. Then, the opening 4 is detached from the sampling spot, and then the force of pressing with a finger is weakened to release the applied pressure. Then, the compressed suction pressure generating chamber 1 returns to the original shape due to the elasticity, whereby a suction pressure (a negative pressure) is developed. Due to the developed suction pressure, the sample is retained in the liquid pooling portion 9 is drawn through the drawing channel 2a into the analytical section 3 as shown in FIG. 11(B). The time period required for introducing the sample into the analytical section 3 in such a method is markedly short compared to the time required for drawing a sample by using capillarity. In addition, such a drawing process is hardly affected by properties of the sample such as viscosity. Furthermore, in this drawing process, because the liquid stresses in the liquid pooling portion 9 and the air vent passage 25 are adjusted as described above, a part of the sample 15 remains in the air vent passage 25 as shown in the drawing, so that air inclusion can be prevented. Furthermore, even if excess suction pressure is developed, because the stopper 8 is formed, it is ensured that the sample 15 is introduced into the analytical section 3 without causing a flow of the sample 15 into the suction pressure generating chamber 1. Accordingly, it is not necessary to take care in adjusting the pressing force with a finger. Then, in the analytical section 3, a reaction between a component in the sample 15 and the reagent contained in the reagent film 7 takes place to generate a pigment, whereby a color is developed in the reagent film 7. Then, the device in which a color is developed in the reagent film 7 is set in a predetermined position in an optical measuring apparatus such as a densitometer. Then, light is irradiated into the device through the window 10 formed in the under surface of the device, so that when using the densitometer, a reflected light is detected in a detecting section to measure the color developed the regent film. Furthermore, in this measuring, when both the whole analytical section 3 and the reagent film 7 are transparent, analysis can also be conducted by using a transmitted light.

EXAMPLE 8

Figure 12:
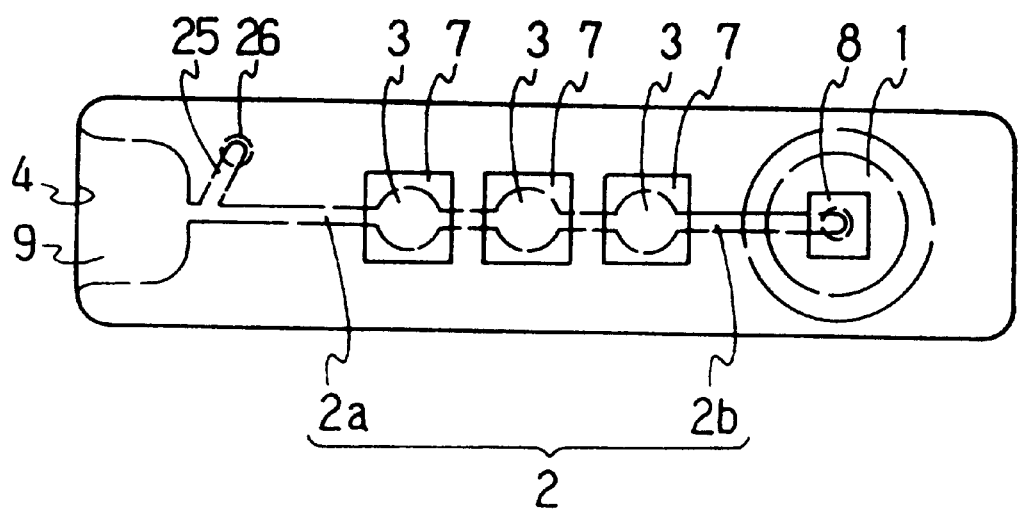
FIG. 12 is a plan view of still another embodiment of the device of the present invention.

FIG. 12 shows a plan view of an embodiment of a device for multiple analysis provided with a plurality of analytical sections arranged in series.

As shown in the drawing, this device is provided with three analytical sections 3 in certain positions in a drawing channel 2, and a reagent film 7 is disposed in each of the analytical sections 3. The respective reagent films 7 are impregnated with different types of reagents. The structure of the device other than these aspects is the same as that of the device shown in FIG. 9, and the same parts as in FIG. 9 are referred to by using the same signs.

This device can be produced by laminating a plurality of films having predetermined shapes and then integrating them together, as in the predescribed device in Example 7, and the method for producing the device, used materials, and the like are also the same as in the device in Example 7. Furthermore, the overall dimensions of the device are usually 15 to 100 mm in length, 5 to 20 mm in width, and 1 to 3 mm in thickness. Furthermore, the whole length of the drawing channel 2 is usually 20 to 80 mm, and the spacing between the analytical sections is usually 3 to 10 mm. The dimensions in other parts of the device are the same as in the device of Example 7.

Although a device provided with three analytical sections is described in this embodiment, the present invention is not limited to such a device, and any number of analytical sections can be provided depending upon the desired number of items for measurement.

Next, a method for analysis using such a device for multiple analysis is performed, for example, as follows.

First, a suction pressure generating chamber 1 of the device is compressed by pressing as in the predescribed embodiment. Then, in this state, the opening 4 is contacted with a sample in a predetermined sampling spot, whereby the sample is drawn by capillarity into the liquid pooling portion 9 where it is retained. Then, the opening 4 is detached from the sampling spot, and thereafter the pressure applied to the suction pressure generating chamber 1 is released, so that a suction pressure is developed. Accordingly, the sample is introduced into the respective three analytical sections 3 one after another, where respective reactions between compounds in the sample and the reagents contained in the respective reagent films 7 take place. Then, the device is set in a predetermined position in an optical measuring apparatus capable of performing multiple analysis. Then, light is irradiated through the window formed in the under surface of the device, whereby the colors developed in the respective reagent films 7 are measured. An example of the optical measuring apparatus is a densitometer. Thus, by using such a device for multiple analysis, a plurality of items can be measured simultaneously.

EXAMPLE 9

Figure 13:
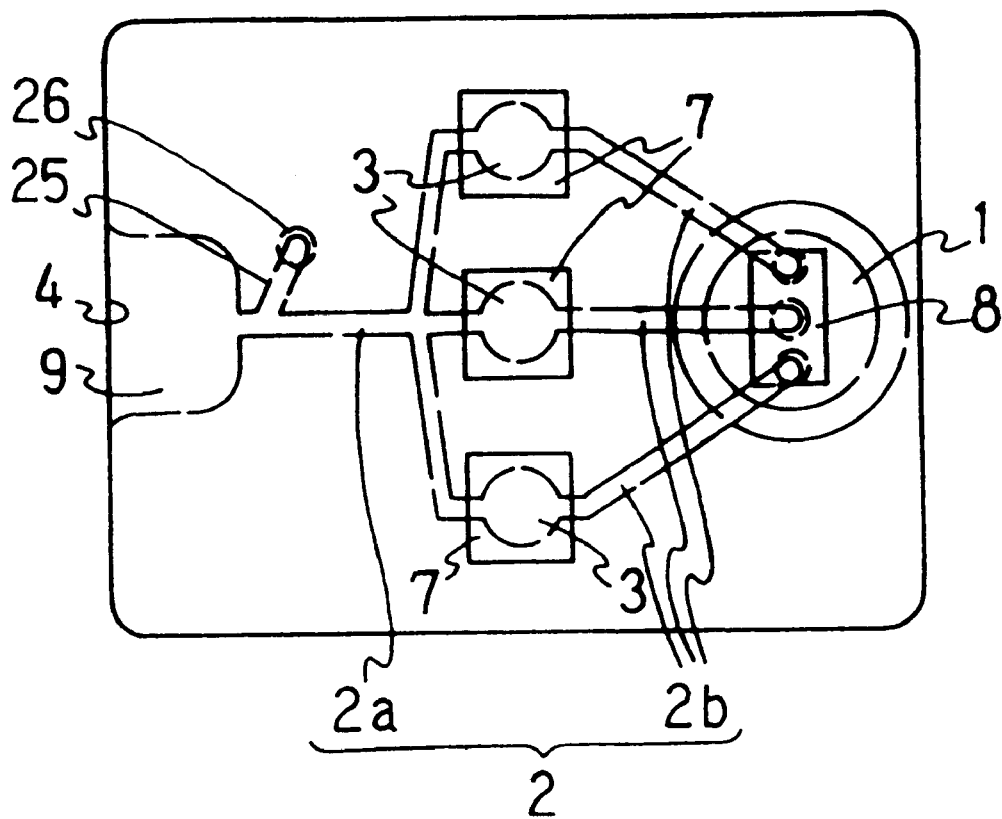
FIG. 13 is a plan view of still another embodiment of the device of the present invention.

FIG. 13 shows a plan view of a device for analyzing a sample for multiple analysis provided with a plurality of analytical sections arranged in parallel.

As shown in the drawing, this device has three drawing channels 2. An analytical section 3 is formed in each of the drawing channels 2, where a reagent film 7 is disposed. Each reagent film 7 is impregnated with a type of reagent different to each other. The portions of each of the three respective drawing channels 2 which extend from the three respective analytical sections 3 toward the opening 4 merge to form a drawing channel 2a in a certain position before reaching the liquid pooling portion 9. Furthermore, three drawing channels 2b extend from a suction pressure generating chamber 1 and are in communication with the three analytical sections 3, respectively. This device and the device shown in FIG. 9 in Example 7 have the same structure other than these characteristics, therefore, the same parts are referred to by using the same signs.

This device can be produced by laminating a plurality of films having predetermined shapes and then integrating them together, as in the predescribed device in Example 7, and the method for producing the device, the materials used, and the like are also the same as those in Example 1. Furthermore, the overall dimensions of the device are usually 15 to 60 mm in length, 10 to 50 mm in width, 1 to 3 mm in thickness. Furthermore, the overall length of the drawing channel 2 is usually 10 to 40 mm, and the spacing of the analytical sections 3 to each other is usually 3 to 10 mm. The dimensions of other parts of the device are the same as in the device of Example 7.

Although a device provided with three analytical sections is shown in this embodiment, the present invention is not limited to this device, and any number of analytical sections and drawing channels can be provided depending upon the desired number of items for measurement.

Next, an analysis using such a device for multiple analysis is performed, for example, as follows.

First, a suction pressure generating chamber 1 of the device is compressed by pressing as in the predescribed embodiment. In this state, the opening 4 is contacted with a sample in a predetermined sampling spot, and the sample is introduced by capillarity into the liquid pooling portion 9, where it is retained. Then, the opening 4 is detached from the sampling spot, and thereafter the pressure applied to the suction pressure generating chamber 1 is released so that a suction pressure is developed. As a result, the sample is introduced into each of the three analytical sections 3 simultaneously, where reactions between components in the sample and the reagents contained in the respective reagent films 7 take place. Then, the device is set in a predetermined position in an optical measuring apparatus capable of performing multiple analysis. Then, light is irradiated through the window formed in the under surface of the device, whereby the color developed in the respective reagent films 7 is measured. Thus, by using such a device for multiple analysis, a plurality of items can be measured simultaneously. An example of the optical measuring apparatus is a densitometer.

Having described the devices for multiple analysis in Example 8 and Example 9, whether the analytical sections are arranged either in series or in parallel may be determined by various conditions such as influence of the reagents to each other, the shapes of the device, or the like.

EXAMPLE 10

Figure 14:
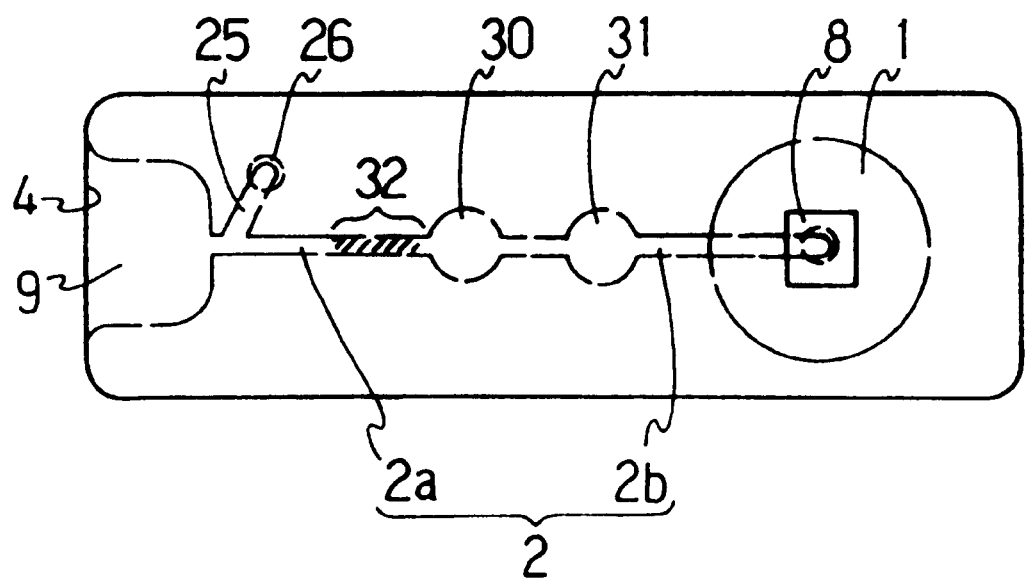
FIG. 14 is a plan view of still another embodiment of the device of the present invention.

FIG. 14 shows a plan view of a device for analyzing a sample in which a reagent positioning section, reagent reaction section, and a measuring section are provided independently in certain positions in the drawing channel.

As shown in the drawing, this device is provided with a reagent positioning section 32, a reagent reaction section 30, and a measuring section 31, each of them being formed in a certain position in a drawing channel 2. The shape of the drawing channel does not particularly change due to the reagent positioning section 32, and a reagent is simply disposed in the drawing channel. Also, it may be a depressed cylindrical shaped cavity like the reagent reaction section. Moreover, the reagent can be disposed by simply positioning the reagent in the channel. or attaching the reagent to the reagent positioning section by using a hydrophilic polymer or the like. Examples of the reagents include wet-type reagents or the like capable of moving together with a sample. More particularly, example of such reagents are, GOD, peroxidase (POD), 4-aminoantipyrine, N-ethyl-N-(2-hydroxyne-3-sulfopropyl)-3-methylaniline (TOOS) and the like. Moreover, even a dry-type reagent can move together with a sample if it can be dissolved in a sample. Furthermore, the reagent reaction section 30 is formed in a same way as in the predescribed embodiment other than that a reagent film is not disposed therein. Furthermore, the measuring section 31 is formed into a depressed cylindrical shaped cavity like the reagent reaction section 30, except that it is made transparent for permitting light entrance. Moreover, an absorbent member such as a filter paper may be disposed in the measuring section 31 in order to fix the transferred pigment. This device and the device shown in FIG. 9 in Example 7 have the same structure other than these characteristics, therefore the same parts are referred to by using the same signs. Moreover, the reagent reaction section 30 may also serve as a measuring section like in Example 7, and in such a case, the reagent reaction section 30 is made transparent for permitting light entrance.

This device for analyzing a sample can be produced by laminating a plurality of films having predetermined shapes and then integrating them together, as in the predescribed embodiment in Example 7. In addition, the method for producing such a device, the materials used, and the like are also the same as those in Example 7. Furthermore, generally a reagent is prepositioned by using a hydrophilic polymer or the like during lamination process of the films. Furthermore, the overall dimensions of the device are usually 15 to 100 mm in length, 5 to 20 mm in width, and 1 to 3 mm in thickness. Furthermore, the overall length of the drawing channel 2 is usually 20 to 80 mm, and the spacing between the reagent positioning section, the reagent reaction section 30, and the measuring section 31 to each other is usually 3 to 10 mm. The dimensions of other parts of the device are the same as in the embodiment in Example 7.

Next, an analysis using such a device for multiple analysis is performed, for example, as follows.

First, a suction pressure generating chamber 1 is compressed by pressing as in the predescribed embodiment. In this state, the opening 4 is contacted with a sample in a predetermined sampling spot, and the sample is drawn by capillarity into the liquid pooling portion 9, where it is retained. Then, the opening 4 is detached from the sampling spot, and thereafter the pressure applied to the suction pressure generating chamber 1 is released so that a suction pressure is developed. As a result, the sample is transferred into the reagent positioning section 32, into the reagent reaction section 30, and then into the measuring section 31 in this order. Then, the sample first moves into the reagent reaction section 30 with the reagent present in the reagent positioning section 32, where a reaction between a component in the sample and the reagent takes place to generate a pigment. The pigment may be produced in a portion between the reagent reaction section 30 and the measuring section 31. Then, the pigment moves to the measuring section 31. If a filter paper is positioned in the measuring section 31, a color is developed in the filter paper. Then, the device is set in a predetermined position in an optical measuring apparatus. Then, light is irradiated into the measuring section, whereby the color of the pigment or the color developed in the filter paper is measured by using an optical measuring apparatus such as a densitometer. As a condition of this measurement, when using the predescribed reagents such as GOD, this measuring should be performed one minute after the reaction with a wavelength of 570 nm.

EXAMPLE 11

Figure 15:
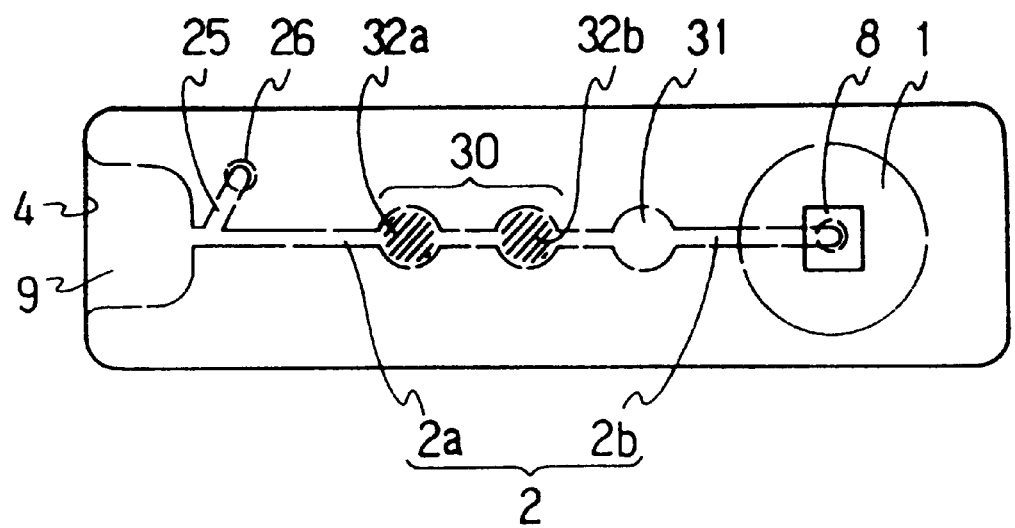
FIG. 15 is a plan view of still another embodiment of the device of the present invention.

FIG. 15 shows a plan view of a device for analyzing a sample in which two reagent positioning sections are provided in certain positions in the drawing channel.

As shown in the drawing, this device is provided with a first reagent positioning section 32a and a second reagent positioning section 32b formed in certain positions in a drawing channel 2, the two sections forming the reagent reaction section 30, and further provided with a measuring section 31. Usually, a first reagent is disposed in the first reagent positioning section 32a, and a second reagent is disposed in the second reagent positioning section 32b.

Although the first reagent positioning section 32a and the second reagent positioning section 32b are formed into depressed cylindrical shaped cavities, reagents may be simply disposed in the drawing channel 2 without changing the shape of the channel, as described later. Furthermore, in disposing the reagents, the reagents may be attached to the reagent positioning sections by using a hydrophilic polymer or the like, while it may be simply positioned as in the predescribed device in Example 10. Suitable reagents are those comprising two or more components which cannot be mixed prior to a reaction with a sample, as previously described. An example of such a reagent is an enzyme-substrate type reagent, specifically, trypsin-substrate type reagent. The substrate usually generates a pigment through an enzyme reaction.

Furthermore, when dissolved and mixed in a sample, this reagent is capable of moving.

Also, the measuring section 31 is formed as a depressed cylindrical shaped cavity like the reagent positioning section. Further, an absorbent member such as a filter paper may be disposed in the measuring section 31 in order to fix the transferred pigment. This device and the device shown in FIG. 9 in Example 7 have the same structure other than these characteristics, therefore, the same parts are referred to by using the same signs. Moreover, a reagent reaction section may serve as a measuring section like in Example 7. In case of this embodiment, the second positioning disposed section 32b may serve as the measuring section 31.

This device can be produced by laminating a plurality of films having predetermined shapes and then integrating them together, as in the predescribed device in Example 7. In addition, the method for producing such a device, the materials used, and the like in this device are also the same as those in Example 7. Furthermore, generally a reagent is prepositioned by using a hydrophilic polymer or the like during lamination process of the films. Furthermore, the overall dimensions of the device are usually 15 to 100 mm in length, 5 to 20 mm in width, and 1 to 3 mm in thickness. Furthermore, the overall length of the drawing channel 2 is usually 20 to 80 mm, and the spacing between the reagent positioning sections and the measuring section is usually 3 to 10 mm. The dimensions of other parts of the device are the same as in Example 7.

Next, an analysis using this device is performed, for example, as follows.

First, as in the predescribed embodiment, a suction pressure generating chamber 1 is compressed by applying pressure. In this state, the opening 4 is contacted with a sample in a predetermined sampling spot, and the sample is drawn by capillarity into the liquid pooling portion 9 to be retained. Then, the opening 4 is detached from the sampling spot, and then the pressure applied to the suction pressure generating chamber 1. is released so that a suction pressure is developed. As a result, the sample is transferred into the first reagent positioning section 32a, into the second reagent positioning section 32b, and into the measuring section 31 in this order. Then, the sample first moves into the second reagent positioning section 32b with the first reagent present in the first reagent disposed section 32a, where the three of the sample, the first reagent, and the second reagent are reacted to each other to generate a pigment. The pigment may be generated in a portion between the second reagent disposed section 32b and the measuring section 31. Then, the pigment moves to the measuring section 31 When a filter paper is positioned in the measuring section 31, a color is developed in the filter paper. Then, the device is set in a predetermined position in an optical measuring apparatus. Then, light is irradiated into the measuring section 31, whereby the color of the pigment or the color developed in the filter paper is measured by using an optical measuring apparatus such as a densitometer.

EXAMPLE 12

Figure 16:
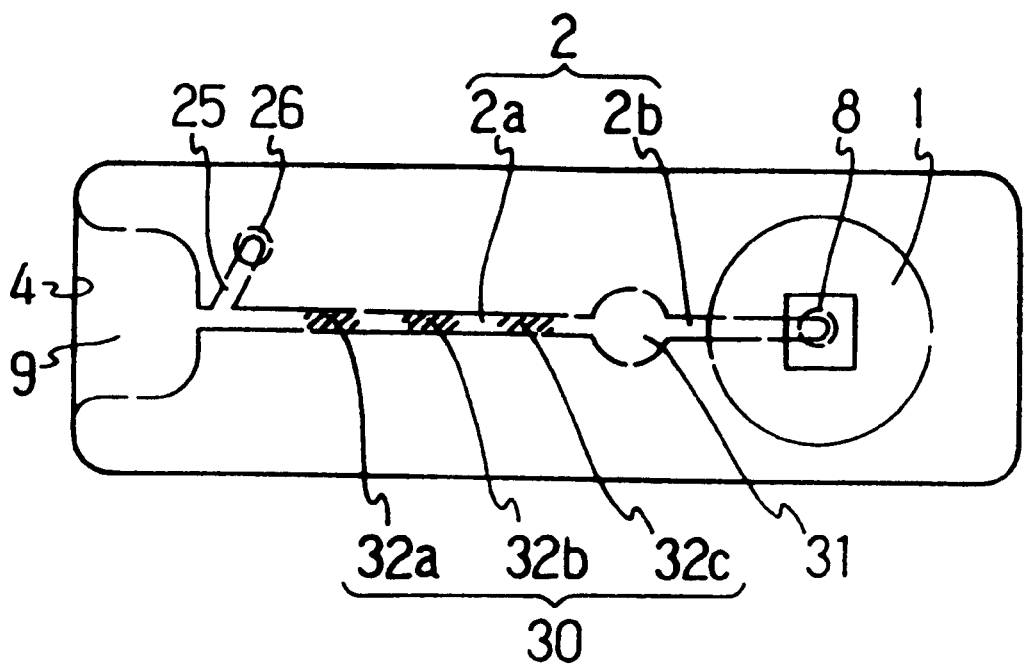
FIG. 16 is a plan view of still another embodiment of the device of the present invention.

FIG. 16 shows a plan view of a device for analyzing a sample in which three reagent positioning sections and a measuring section are provided in certain positions in a drawing channel. This device has a structure in which those in Example 10 and 11 are integrated.

As shown in the drawing, this device is provided with a first reagent positioning section 32a, a second reagent positioning section 32b, and a third reagent positioning section 32c formed in certain positions in a drawing channel 2, all of these forming a reagent reaction section 30 in combination, and further provided with a measuring section 31 formed in a certain position in-the drawing channel 2. Usually, a first-reagent is disposed in the first reagent positioning section 32a, a second reagent is disposed in the second reagent positioning section 32b, and a third reagent is disposed in the third reagent positioning section 32c.

The reagents are simply disposed in the respective three reagent positioning sections 32a, 32b, and 32c without changing the shape of the drawing channel 2. Furthermore, in disposing the reagents, they may be simply disposed in the drawing channel as in the device previously described in Example 4, or alternatively, the reagents may be attached to the respective reagent positioning sections by using a hydrophilic polymer or the like. Suitable reagents are those comprising two or more components which cannot be mixed prior to a reaction with a sample as previously described. Examples of such a reagent include enzyme-substrate type reagents, for example, a reagent comprising a trypsin, the substrate of the trypsin, and a buffer solution. By using such a reagent, for example, a trypsin inhibitor in urine can be measured. Furthermore, a pigment is generated through a reaction between the substrate and the enzyme. With regard to this reagent, the first reagent is the buffer solution, the second reagent is the trypsin, and the third reagent is the substrate. Besides, when dissolved and mixed in a sample, this reagent is capable of moving.

The measuring section 31 is formed as a depressed cylindrical shaped cavity. An absorbent member such as a filter paper may be disposed in the measuring section 31 in order to fix the transferred pigment. The structure of this device other than these characteristics is the same as that of the device shown in FIG. 9 in Example 7, therefore the same parts are referred to by using the same signs.

This device can be produced by laminating a plurality of films having predetermined shapes and then integrating the films together, as in the device described in Example 7. In addition, the method for producing such a device, the materials used, and the like are also the same as those in Example 7. Furthermore, the reagents are generally disposed in advance by using hydrophilic polymers or the like during the process of laminating the films. Furthermore, the overall dimensions of the device are usually 15 to 100 mm in length, 5 to 20 mm in width, and 1 to 3 mm in thickness. Furthermore, the whole length of the drawing channel 2 is usually 20 to 80 mm, and the spacing between the reagent positioning sections and the measuring section is usually 3 to 10 mm. The dimensions of other parts of the device are the same as in Example 7.

Next, a method for analyzing a sample by using this device will be described by referring to a case using the predescribed reagent comprising a buffer solution, a trypsin and a substrate.

First, the device for analyzing a sample having a buffer solution in the first reagent positioning section 32a, a trypsin in the second reagent positioning section 32b, and a substrate in the third reagent positioning section 32c is prepared. Then, as in the predescribed embodiment, a suction pressure generating chamber 1 is compressed by applying a pressure, and in this state, the opening 4 is contacted with a sample (urine) in a predetermined sampling spot, so that the sample is drawn by capillarity into the liquid pooling portion S to be retained. Then, the opening 4 is detached from the sampling spot, and then the pressure applied to the suction pressure generating chamber 1 is released so that a suction pressure is developed. As a result, the sample is transferred into the first reagent positioning section 32a, into the second reagent positioning section 32b, into the third reagent positioning section 32c, and into the measuring section 31 in this order. Then, the sample moves into the second reagent positioning section 32b with the buffer solution present in the first reagent positioning section 32a, where the sample, the buffer solution, and the trypsin are mixed together. Then, the mixture is transferred into the third reagent positioning section 32c, where it is mixed with the substrate, whereby an enzyme reaction is caused to generate a pigment. Moreover, the pigment may be generated in a position between the third reagent positioning section 32c and the measuring section 31. Then, the pigment moves to the measuring section 31. Therefore, when a filter paper is positioned in the measuring section 31, a color is developed in the filter paper. Then, the device is set in a predetermined position in an optical measuring apparatus. Then, light is irradiated into the measuring section 31, whereby the color of the pigment or the color developed in the filter paper is measured by using an optical measuring apparatus such as a densitometer.

EXAMPLE 13

Next, an embodiment of a device for analyzing a sample of the present invention in which a vent is formed in a suction pressure generating chamber will be described.

FIG. 17 shows a cross-sectional view of an embodiment of this device. As shown in FIG. 17(A), the basic structure of the device is the same as that of the device shown in FIG. 9 in Example 7, and the same parts are referred to by using the same signs. The vent 1a is usually 0.1 to 5 mm in diameter. An analysis of a sample by using this device is conducted, for example, as follows.

Figure 17A:
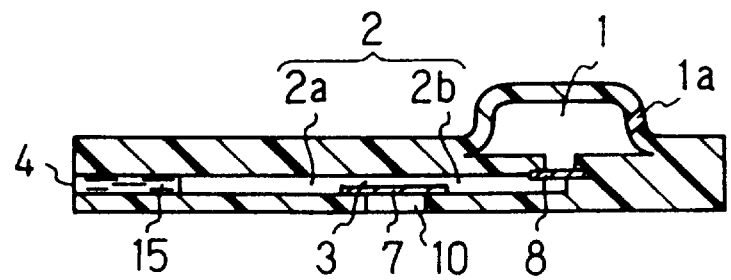
FIG. 17(A)–(D) are cross-sectional views showing a process for drawing a sample in a still another embodiment of the device of the present invention.
Figure 17B:
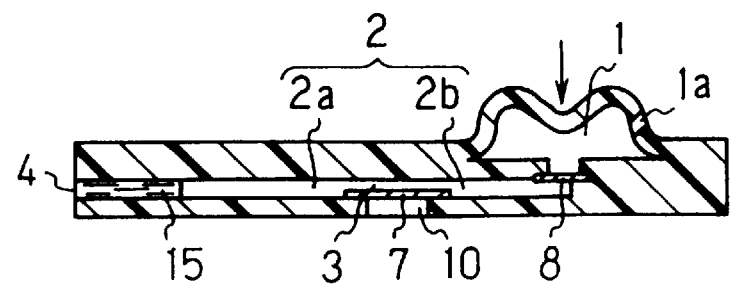
Figure 17C:
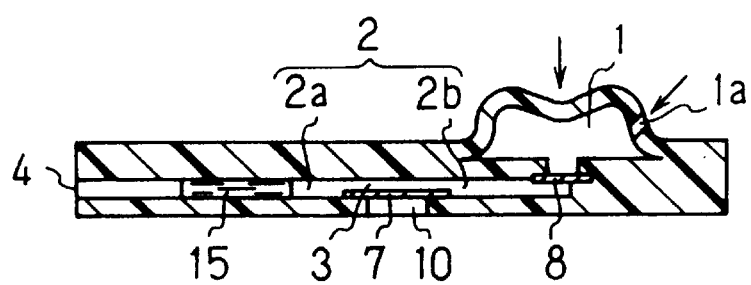
Figure 17D:
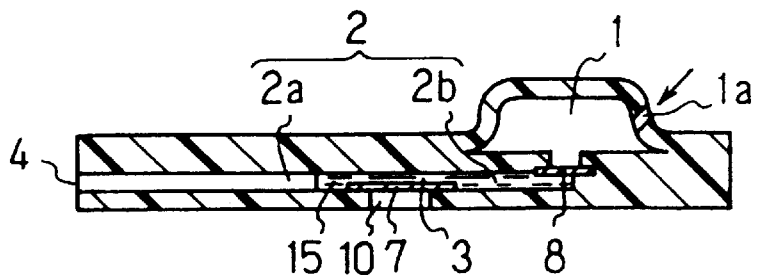

First, the opening 4 of the device is contacted with a sample, so that the sample 15 is retained in the liquid pooling portion 9. Then, as shown in FIG. 17(B), the suction pressure generating chamber 1 is pressed with a finger or the like. At this time, because the air in the suction pressure generating chamber 1 is discharged through the vent 1a, the sample is not discharged through the opening 4 by the air forced from the suction pressure generating chamber 1. Then, as shown in FIG. 17(C), the vent 1a is closed with a finger or the like when the suction pressure generating chamber 1 is compressed. Then, when the pressure applied to the suction pressure generating chamber 1 is released in a state in which the vent 1a is closed as shown in FIG. 17(D), the suction pressure generating chamber 1 returns to its original shape and thereby a suction pressure is developed. As a result, the sample 15 is transferred through the drawing channel 2 into the analytical section 3. The subsequent analyzing operation is the same as in Example 7.

Accordingly, by using such a device in which the suction pressure generating chamber 1 is provided with the vent 1a, it is possible to apply a pressure to the suction pressure generating chamber 1 after the opening 4 is contacted with the sample 15 and the sample is retained in the liquid pooling portion. As a result, sampling can be performed easily.

EXAMPLE 14

Next, an embodiment of a device of the present invention in which a suction pressure generating tube is used as a suction pressure generating means will be described.

FIG. 18 shows a cross-sectional view of an embodiment of such a device for analyzing a sample. As shown in FIG. 18(A), this device has the same structure as that of the device shown in FIG. 9 in Example 7, except that a suction pressure generating tube 21 is provided in place of a suction pressure generating chamber, and the same parts are referred to by using the same signs. The suction pressure generating tube 21 can be formed, for example, by placing a resin sheet, which is bent so that the shape of a cross-section of the sheet in longitudinal direction becomes approximately a reverse U-shaped, on the body of the device. In this case, one end of the suction pressure generating tube communicates through a stopper 8 which is gas-permeable and liquid-impermeable with the drawing channel 2, and the other end is closed. In the suction pressure generating tube, usually the sheet is 0.01 to 2 mm in thickness, and the tube is 0.5 to 5 mm in height on the inside, 1 to 10 mm in width on the inside, and 5 to 30 mm in length. It is desired that the suction pressure generating tube 21 is formed so that it may not overlap with the drawing channel 2, an analytical section 3, or the like. This because it is necessary to compress the tube by applying a pressure through a hand in order to develop a suction pressure by the suction pressure generating tube 21, and there is a possibility that the shape of the drawing channel or the like might be changed by the pressure. Suitable materials for the resin sheet are, for example, soft vinyl chloride resin, soft silicon resin, natural rubber, and the like. Furthermore, the shape of a cross section of the suction pressure generating tube in a longitudinal direction is not limited to said reverse U-shape. For example, it may be rectangular or the like.

Figure 18A:
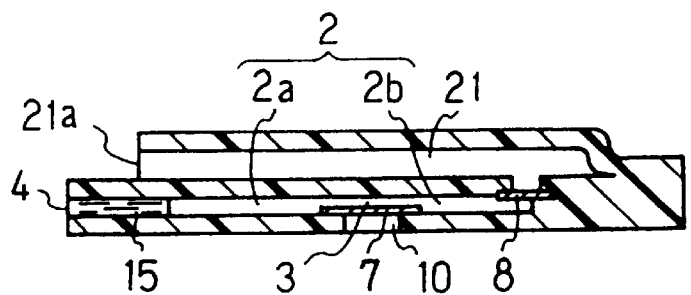
FIG. 18(A)–(D) are cross-sectional views showing a process for drawing a sample in a still another embodiment of the device of the present invention.
Figure 18B:
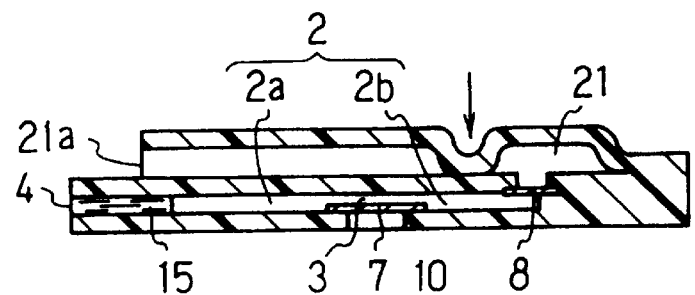
Figure 18C:
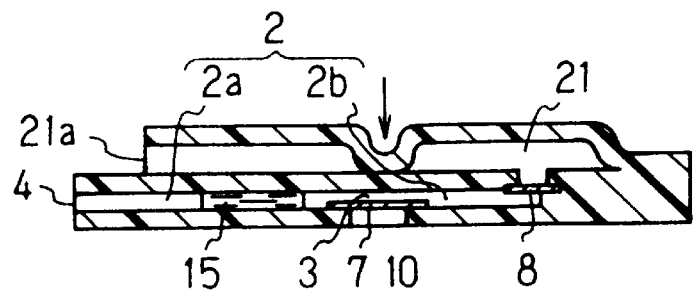
Figure 18D:
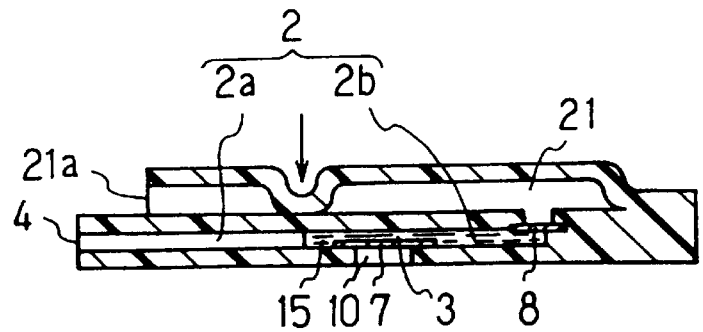

A sample may be analyzed by using this device, for example, as in the following steps. First, the opening 4 of the device is contacted with a sample, so that the sample 15 is retained in a liquid pooling portion 9. Then, as shown in FIG. 18(B), a portion of the suction pressure generating tube 21 on one end side (right end in the drawings) in communication with the drawing channel 2 is pressed with a finger or the like, whereby the corresponding portions of the sheet are adhered to each other. Then, as shown in FIG. 18(C) and FIG. 18(D) successively, the tube can be drawn by moving the pressing portion toward the open end. As a result, a suction pressure is developed in the suction pressure generating tube 21, whereby the sample 15 is moved through the drawing channel 2 into the analytical section 3. Subsequent analyzing operation is conducted in the same way as in Example 7.

Accordingly, by using such a device having the suction pressure generating tube as the suction pressure generating means, a sucking operation can be performed after the opening 4 is contacted with the sample 15, which is then retained in the liquid pooling portion, as in the device provided with a suction pressure generating chamber having the vent 1a. As a result, sampling can be operated more easily.

EXAMPLE 15

Next, an embodiment of the present invention where a sample is analyzed by an electrochemical means will be described.

Figure 19A:
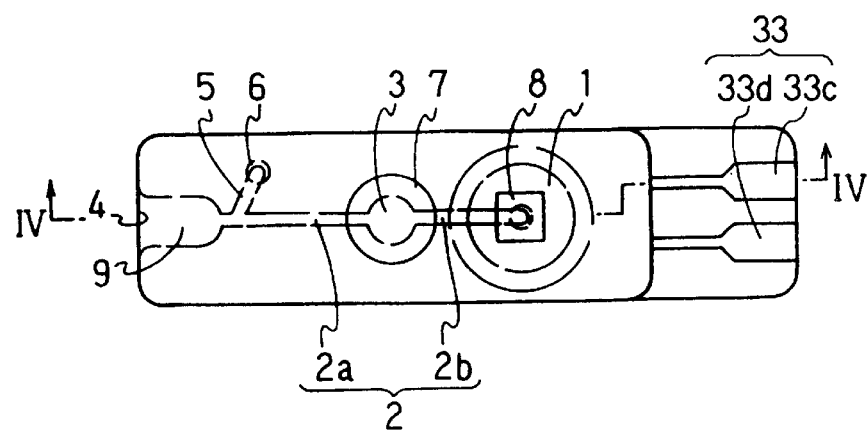
FIG. 19(A) is a plan view showing a still another embodiment of the device of the present invention.
Figure 19B:
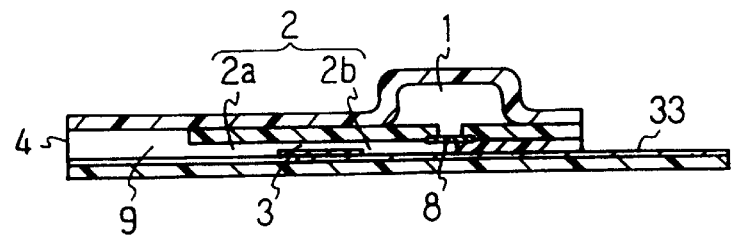
Figure 19(B) is a cross-sectional view of the device of the FIG. 19(A) taken along the line IV—IV.

FIG. 19 shows a device for analyzing a sample provided with electrodes. FIG. 19(A) is a plan view of the device, and FIG. 19(B) is a cross-sectional view of the device shown in FIG. 19 (A) taken along the line IV—IV . The device shown in these drawings has the same structure as the device in Example 7, except that the electrodes are formed and no window is formed, therefore the same parts are referred to by using the same signs.

As shown in the drawings, the electrodes comprise a working electrode 33a and a counter electrode 33b, which are formed under the analytical section 3. Both of the electrodes extend beyond the suction pressure generating chamber 1, and the ends of them are formed into terminals 33c and 33d, respectively.

Figure 20:
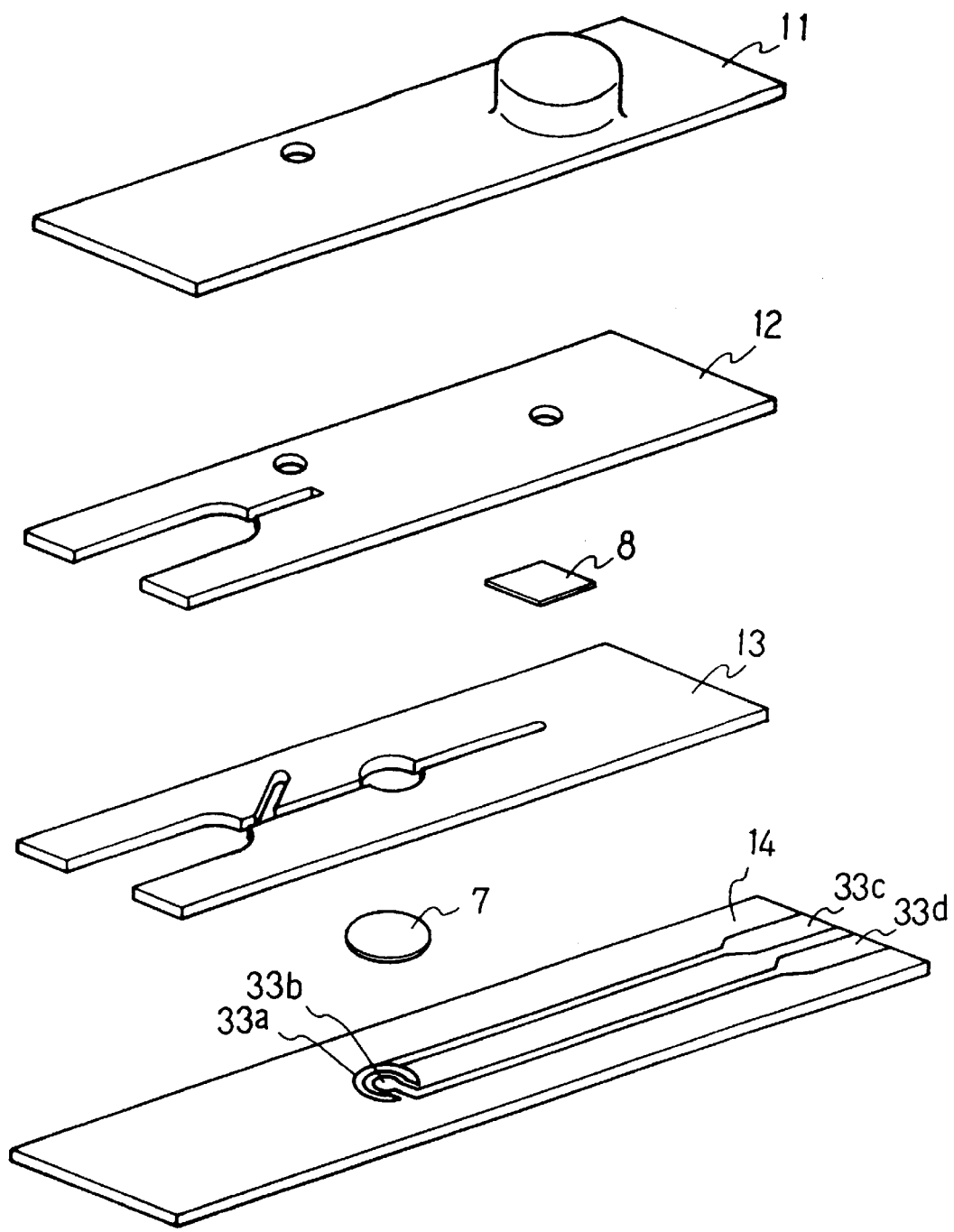
FIG. 20 is a perspective view showing the fabrication of the device shown in FIG. 19.

This device can be produced by laminating the films formed into respective predetermined shapes as in Example 7. For example, as shown in FIG. 20, the device can be produced by laiminating films 11, 12, 13, and 14 formed into respective type of shapes, with a reagent film 7 and a hydrophobic porous film 8 positioned therebetween.

The film 14 forms the under side portion of the device, and the electrodes (33a, 33b, 33c, 33d) are formed on the upper surface of the film. The electrodes can be formed, for example by printing the terminals (33c and 33d) on the film by screen printing using silver (Ag) paste, while printing the working electrode 33a and the counter electrode 33b by screen printing using conductive carbon paste. The dimensions of the electrodes are, for example, in case of the shape shown in the drawing, usually 1 to 14 mm in outer diameter of the working electrode 33a, 3 to 15 mm in outer diameter of the counter electrode 33b, and 0.5 to 2 mm in width of the spacing between these electrodes Furthermore, the overall length of the electrode including the terminals is 10 to 50 mm. Moreover, the shapes of the electrodes are not limited to the shapes shown in the drawing. The material for the film is not particularly limited as long as it has insulating property, and for example, PET, polypropylene, polyester or the like may be used. Furthermore, a hole to form a window is not formed in the film 14. Furthermore, the film 14 is not necessarily transparent, and it may be colored.

In producing this device, a reagent film 7 produced independently may be used, or alternatively, the reagent film 7 may be directly formed on the electrodes (the working electrode and the counter electrode). For example, the reagent film can be formed by applying a hydrophilic high polymer aqueous solution on the electrodes portion followed by drying, thereupon further applying a reagent solution followed by drying. An example of the high polymer aqueous solution is a 0.5% by weight aqueous solution of carboxymethyl cellulose. In case of analyzing lactic acid, for example, a suitable reagent solution is 400 U/ml of lactate oxidase and 2.0% by weight aqueous solution of potassium ferricyanide. Furthermore, in case of analyzing glucose, glucose oxidase may be used in place of said lactate oxidase, and in case of analyzing cholesterol, cholesterol oxidase may be used in place of said lactate oxidase.

Next, a method for analyzing a sample by using this device will be described. First, as in the predescribed embodiments, the suction pressure generating chamber 1 is compressed, and in this state, the opening 4 is contacted with a sample in a predetermined sampling spot, thereby the sample is drawn by capillarity into the liquid pooling portion 9 to be retained. Then, the pressure applied to the suction pressure generating chamber 1 is released to develop a suction pressure, whereby the sample is moved into the reagent film 7 positioned in the analytical section 3, where a reaction with the reagent takes place. Then, the device is set in a predetermined position in an electrochemical measuring apparatus, and after a reaction of a predetermined time period, a certain amount of voltage is applied between the working electrode and the counter electrode, and the flowing electric current is measured.

EXAMPLE 16

Next, an embodiment of the present invention in which a device of the present invention is used in an analysis using immunoassay will be described.

Figure 21A:
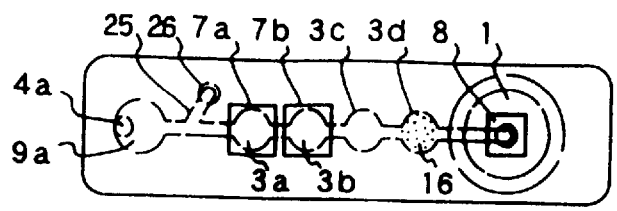
FIG. 21(A)–(H) are plan views showing an analysis using a still another embodiment of the device of the present invention.
Figure 21B:
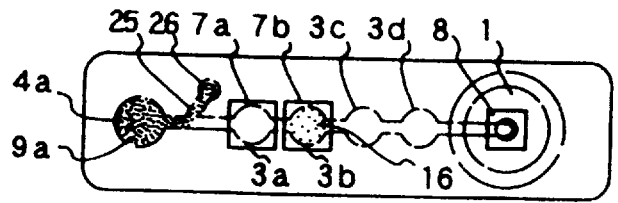
Figure 21C:
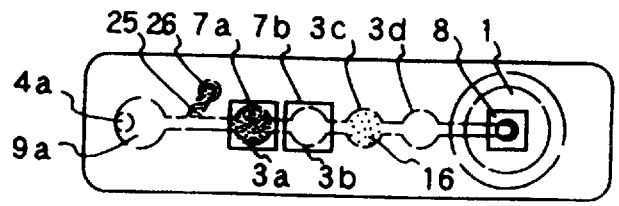
Figure 21D:
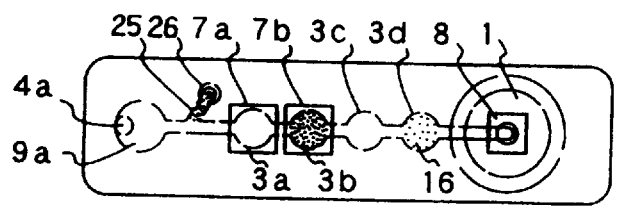
Figure 21E:
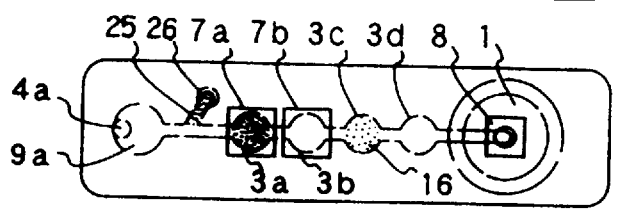
Figure 21F:
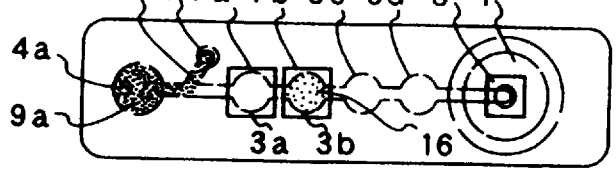
Figure 21G:
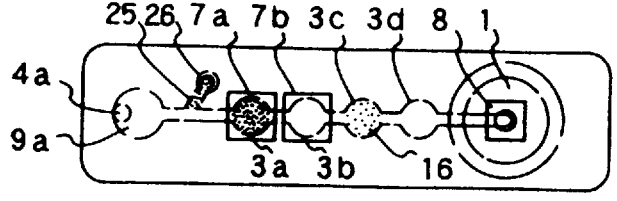
Figure 21H:
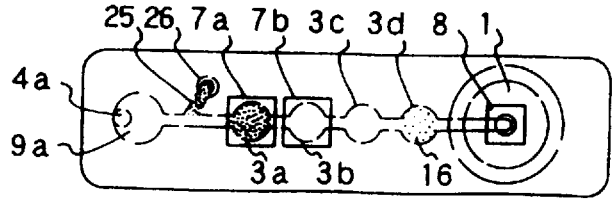
Figure 22:
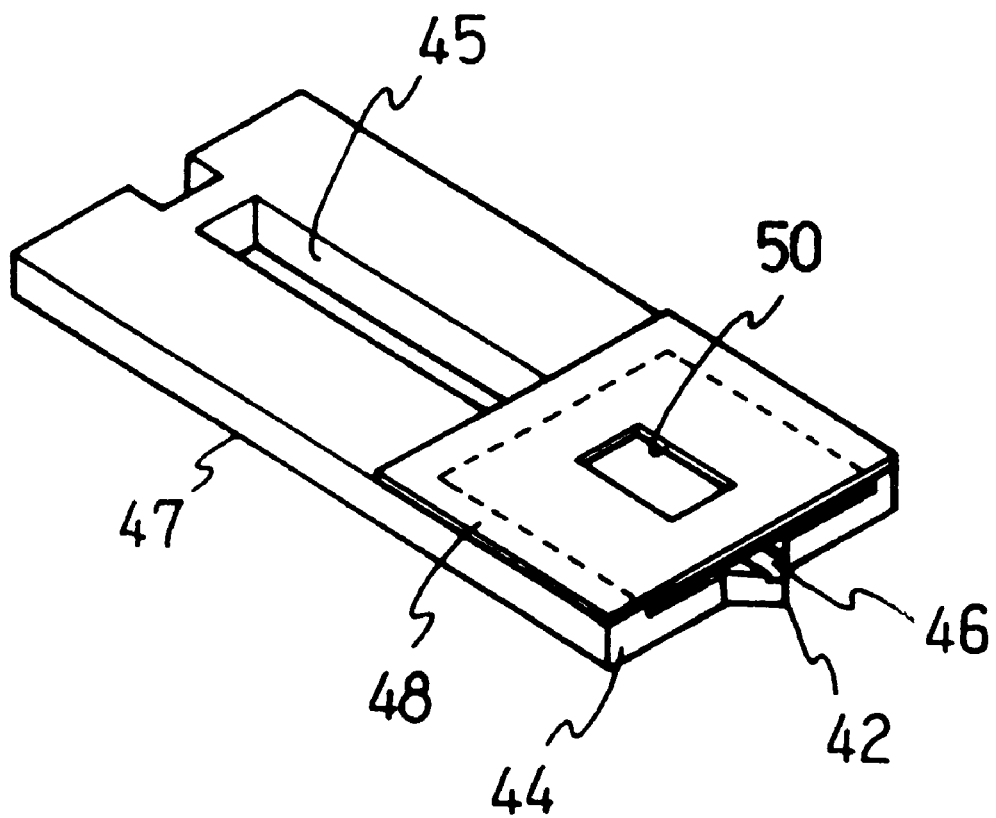
FIG. 22 is a perspective view of a conventional device for analyzing a sample.

FIG. 21(A) shows a plan view of a device for analyzing a sample for immunoassay. As shown in the drawing, in this device, a liquid pooling portion 9a is formed as a depressed cylindrical shaped cavity, and a circular opening 4a is formed thereon. Furthermore, four analytical sections 3a, 3b, 3c, and 3d are formed in certain positions in the drawing channel 2. A reagent film 7a containing an antibody, which is labelled by a colored material such as gold colloid through reaction with a target antigen in a sample (a labelled antibody), is disposed in the analytical section 3a. Furthermore, a reagent film 7b, where an antibody which reacts with the same antigen mentioned above is immobilized, is disposed in the analytical section 3b. Furthermore, a rinsing solution 16 is disposed in the analytical section 3d. The rest of the structure is the same as in the device shown in FIG. 9 in Example 7, therefore the same parts are referred to by using the same signs.

Immunoassay using this device is performed, for example, as shown in FIG. 21(B)–(H). First, the suction pressure generating chamber 1 is compressed by pressing, and in this state, the opening 4a is contacted with a sample, whereby the sample is drawn by capillarity into the liquid pooling portion 9a to be retained (FIG. 21(B)). At this time, the rinsing solution 16 is forced to move into the analytical section 3b by the air discharged from the suction pressure generating chamber. Then, the pressing force applied to the suction pressure generating chamber 1 is slightly weakened to develop a weak suction pressure, thereby the sample is moved into the analytical section 3a, where a reaction between the antigen in the sample and the labelled antibody takes place (FIG. 21(C)). At this time, the rinsing solution is moved into the analytical section 3c by the suction pressure. Then, when the pressure applied to the suction pressure generating chamber 1 is completely released to develop a suction pressure, the sample is moved into the analytical section 3b, where the antigen in the sample is reacted with the immobilized antibody (FIG. 21(D)). Furthermore, at this time, the rinsing solution 16 is moved into the analytical section 3d. Then, the suction pressure generating chamber 1 is lightly compressed again, and the resulting discharged air forces the sample to move into the analytical section 3a (FIG. 21(E)). Then, the antigens linked to the immobilized antibodies remain in the analytical section 3b, the antigen being labelled by the labelled antibodies. However, a number of labelled antibodies which are not linked to the antigens also remain in the analytical section 3b. At this time, the rinsing solution 16 is transferred into the analytical section 3c. Then, the suction pressure generating chamber 1 is further strongly compressed so that the sample is moved into the liquid pooling portion 9a forced by the discharged air, and also the rinsing solution 16 moved into the analytical section 3b (FIG. 21(F)). Then, the pressure applied to the suction pressure generating chamber 1 is slightly released to generate a weak suction pressure, whereby the rinsing solution 16 is moved to the analytical section 3c (FIG. 21(G)). As a result, the analytical section 3b is rinsed, and only the antigens linked both to the immobilized antibodies and to the labelled antibodies are present in the analytical section 3b. At this time, the sample is transferred into the analytical section 3a. Then, in this state, the amount of the labelled antibodies present in the analytical section Sc is measured by using an optical means. After measuring, the pressure applied to the suction pressure generating chamber 1 is completely released (FIG. 21(H)), and the device is discarded.

Finally, it is to be understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraces therein.

What is claimed is:

1. A device for collecting a sample for analysis, comprising:
   a main body;
   a suction pressure generator;
   a drawing channel formed in the main body in communication with the suction pressure generator, an opening in the main body being formed at the end of said drawing channel distal with respect to said suction pressure generator; and
   an analytical section formed in said drawing channel between the suction generator and the opening, the analytical section communicating directly with the exterior of the device through the drawing channel,
   wherein a gas-permeable and liquid-impermeable stopper is provided in the drawing channel between the suction pressure generator and the analytical section and in use a sample is drawn into the main body through the opening by suction pressure developed by said suction pressure generator, and then the sample is transferred by the suction pressure through the drawing channel into the analytical section.

2. A device as claimed in claim 1, wherein a plurality of analytical sections are formed in the drawing channel, and the stopper is provided in the drawing channel between said suction pressure generating means and the analytical section closest to the suction pressure generating means.

3. A device as claimed in claim 1, wherein the opening has a shape enlarging toward the end.

4. A device as claimed in claim 1, wherein the analytical section formed in the drawing channel serves as a reagent positioning section and a reagent reaction section.

5. A device as claimed in claim 1, wherein the suction pressure generator means is a suction pressure generating tube.

6. A device as claimed in claim 1, wherein a pair of electrodes comprising a working electrode and a counter electrode is provided in at least one analytical section.

7. A device as claims in claim 1, wherein the drawing channel is divided into a plurality of drawing channel members at a position between the opening and the suction pressure generator, each of the drawing channel members being provided with an analytical section and being in communication with the suction pressure generator.

8. A device as claimed in claim 1, wherein the stopper is made from a hydrophobic porous material.

9. A device as claimed in claim 1, wherein the overall length of the device is 15 to 100 mm.

10. A device as claimed in claim 1, wherein the width of the device is 20 to 50 mm.

11. A device as claimed in claim 1, wherein the width of the device is 5 to 20 mm.

12. A device as claimed in claim 1, wherein the overall thickness of the device is 1 to 5 mm.

13. A device as claimed in claim 1 wherein the drawing channel is divided into a plurality of drawing channel members at a position between the opening and the suction pressure generator.

14. A device as claimed in claim 1, wherein the main body is dimensioned to be manipulates hand.

15. A device as claimed in claim 1, wherein the device is designed to be discarded after a single use.

16. A device as claimed in claim 1, wherein a liquid pooling portion is formed between the opening and the drawing channel, and an air vent passage branches from a portion of the drawing channel between the liquid pooling portion and the analytical section, the end of the air vent passage opening to the outside.

17. A device as claimed in claim 16, wherein the liquid flow resistance in the air vent passage is larger than the liquid flow resistance in the liquid pooling portion.

18. A device as claimed in claim 1, wherein a reagent positioning section, a reagent reaction section and an analytical section are provided independently in certain positions in the drawing channel.

19. A device as claimed in claim 18, wherein a plurality of reagent positioning sections are provided in certain positions in the drawing channel.

20. A device as claimed in claim 1, wherein the suction pressure generator means is a suction pressure generating chamber capable of changing its volume.

21. A device as claimed in claim 20, wherein a vent is formed in the suction pressure generating chamber.

22. A device as claimed in claim 1, further comprising a bypass channel formed in the main body and branching from the drawing channel at a position between the analytical section and the opening and in communication with the suction pressure generator, wherein the relationship between a liquid flow resistance (X) in a first portion of the drawing channel between said analytical section and said suction pressure generator, a liquid flow resistance (Y) in the bypass channel and a liquid flow resistance (Z) in a second portion of the drawing channel between the position at which said bypass channel branches and said analytical section satisfies the inequality (X)>(Y)>(Z).

23. A device as claimed in claim 22, wherein the drawing channel is divided into a plurality of drawing channel members at a position between the opening and the suction pressure generator, each of the drawing channel members being provided with an analytical section and being in communication with the suction pressure generator, the bypass channel branching from the drawing channel at a position between the division point and the opening.

24. A device as claimed in claim 1, wherein the suction pressure generator comprises a chamber formed in the main body in communication with the drawing channel.

25. A device as claimed in claim 24, further comprising a flexible cover on the main body, whereby changes in pressure in the chamber of the suction pressure generator are created by movement of the flexible cover.

26. A device as claimed in claim 1, wherein a positive pressure can be generated to return a sample withdrawn from the analytical section to the analytical section.

27. A device as claimed in claim 1, further comprising a bypass channel formed in the-main body and branching from the drawing channel at a position between the analytical section and the opening and in communication with the suction pressure generator.

28. A device as claimed in claim 27, wherein a liquid flow resistance in a first portion of the drawing channel between said analytical section and said suction pressure generator is greater than a liquid flow resistance in the bypass channel and a liquid flow resistance a second portion of the drawing channel between said analytical section and a position at which said bypass channel branches.

* * * * *